(12) United States Patent
Allikmets et al.

(10) Patent No.: US 8,012,683 B2
(45) Date of Patent: Sep. 6, 2011

(54) VARIANTS IN COMPLEMENT REGULATORY GENES PREDICT AGE-RELATED MACULAR DEGENERATION

(75) Inventors: Rando L. Allikmets, Cornwall on Hudson, NY (US); Gregory S. Hageman, Coralville, IA (US); Michael C. Dean, Frederick, MD (US); Albert M. Gold, Frederick, MD (US)

(73) Assignees: University of Iowa Research Foundation, Iowa City, IA (US); The Trustees of Columbia University in the City of New York, New York, NY (US); United States of America, as represented by the Secretary of the Department of Health and Human Services, Washington, DC (US)

( * ) Notice: Subject to any disclaimer, the term of this patent is extended or adjusted under 35 U.S.C. 154(b) by 507 days.

(21) Appl. No.: 11/706,074

(22) Filed: Feb. 13, 2007

(65) Prior Publication Data

US 2008/0261211 A1    Oct. 23, 2008

Related U.S. Application Data

(60) Provisional application No. 60/772,989, filed on Feb. 13, 2006, provisional application No. 60/772,688, filed on Feb. 13, 2006.

(51) Int. Cl.
*C12Q 1/68* (2006.01)
*C12P 19/34* (2006.01)

(52) U.S. Cl. .......................................... 435/6; 435/91.1
(58) Field of Classification Search .................... None
See application file for complete search history.

(56) References Cited

U.S. PATENT DOCUMENTS

| 5,474,796 | A | 12/1995 | Brennan et al. |
| 6,812,339 | B1 | 11/2004 | Venter et al. |
| 2002/0015957 | A1 | 2/2002 | Hageman et al. |
| 2004/0170633 | A1 | 9/2004 | Taylor et al. |
| 2008/0146501 | A1 | 6/2008 | Hageman et al. |
| 2008/0261211 | A1 | 10/2008 | Allikmets et al. |
| 2008/0280825 | A1* | 11/2008 | Hageman et al. ............... 514/12 |

FOREIGN PATENT DOCUMENTS

EP    1996214 A2    12/2008
WO    WO2006/062716 A2    6/2006

(Continued)

OTHER PUBLICATIONS

Gold et al., Variation in factor B (BF) and complement component 2 (C2) genes is associated with age-related macular degeneration, Nature Genetics, Advance ONline Publication, published online Mar. 5, 2006, pp. 1-5.*

(Continued)

*Primary Examiner* — Mark Staples
(74) *Attorney, Agent, or Firm* — Kilpatrick Townsend & Stockton LLP

(57) ABSTRACT

Methods for identifying a subject at risk for developing AMD are disclosed, as are kits which can be used to practice the methods. The methods include identifying specific protective or risk polymorphisms or genotypes from the subject's genetic material, including polymorphisms in the BF, C2 and/or CFH genes. Microarrays and kits for use in these methods are also provided.

10 Claims, 4 Drawing Sheets

FOREIGN PATENT DOCUMENTS

| WO | WO 2007/056111 A1 | 5/2007 |
|---|---|---|
| WO | WO2007/095185 A2 | 8/2007 |
| WO | WO2007/095287 A2 | 8/2007 |
| WO | WO2007/120975 A2 | 10/2007 |

OTHER PUBLICATIONS

Cordoba et al., Translational Mini-Review Series on Complement Factor H: Genetics and disease associations of human complement factor H, Journal compilation © 2008 British Society for Immunology, Clinical and Experimental Immunology, 2008, 151: 1-13.*

Despriet, D., et al, "Complement Factor H Polymorphism Complement Activators, and Risk of Age-Related Macular Degeneration," *JAMA*, Jul. 19, 2006 vol. 296, pp. 301-309.

Dragon-Durey, M., et al., Heterozygous and Homozygous Factor H Deficiencies Associated with Hemolytic Uremic Syndrome or Membranoproliferative Glomerulonephritis: Report and Genetic Analysis of 16 Cases, *J Am Soc Nephrol.* (2004) 15:787-795.

Francis, Peter J., "Haplotypes in the Complement Factor H (CFH) Gene: Associations with Drusen and Advanced Age-Related Macular Degeneration," *PloS One*, 2007 vol. 2, pp. 1-6.

Gotoh, N. et al., "No association between complement factor H gene polymorphism and exudative age-related macular degeneration in Japanese," *Human Genetics*, 2006, 120:139-143.

Hughes, Anne E., et al, "A common CFH haplotype of CFHR1 and CFHR3, is associated with the lower risk of age-related macular degeneration," *Nature Genetics*, Oct. 2006 (E publication Sep. 24, 2006), vol. 38, pp. 1173-1178.

Li, M. et al., "CFH haplotypes without the Y402H coding variant show strong association with susceptibility to age-related macular degeneration," *Nature Genetics*, Sep. 2006, vol. 38, No. 9, pp. 1049-1054.

Magnusson, K. P., et al., "CFH Y402H Confers Similar of Soft Drusen and Both Forms of Advanced AMD," *PLoS Medicine*, vol. 3, Issue e5, pp. 109-113, Jan. 2006.

Mullins, R., et al., "Structure and composition of drusen associated with glomerulonephritis: Implications for the role of complement activation in drusen biogenesis", *Eye* (2001) 15:390-395.

Nicaud, V. et al., "Lack of association between complement factor H polymorphisms and coronary artery disease or myocardial infarction," *Journal of Molecular Medicine*, 2007, 85:771-775.

Tedeschi-Blok, N. et al., "Population-Based Study of Early Age-Related Macular Degeneration, Role of the Complement Factor H Y402H Polymorphism in Bilateral but Not Unilateral Disease," *Ophthalmology*, Jan. 2007, 114:99-103.

PCT Search Report for application No. PCT/US07/03904 of Aug. 1, 2008.

Written Opinion for application No. application PCT/US07/03904 of Aug. 1, 2008.

PCT Search Report for application No. PCT/US07/73514 of Aug. 13, 2008.

Written Opinion for application No. PCT/US07/73514 of Aug. 13, 2008.

Bentley et al., "Isolation of cDNA Clones for Human Complement Component C2," *PNAS*, 81:1212-1215 (1984).

Database Hapmap Project Hompage [Online], retrieved from http://www.hapmap.org/downloads/assay-design_protocols.html, Sep. 25, 2007.

Database Probe [Online] NCBI; Sep. 16, 2005, retrieved from http://www.ncbi.nlm.nih.gov/genome/probe/reports/probereport.cgi?uid=503071, the whole document & Database SNP [Online] NCBI Dec. 3, 2002, retrieved from http://www.ncbi.nih.gov/snp/snp_ss.cgi?subsnp_id=5606986.

Database Probe [Online] NCBI Sep. 16, 2005, retrieved from http://www.ncbi.nlm.nih.gov/genome/probe/reports/probereport.cgi?uid=501784, the whole document & Database SNP [Online] NCBI Dec. 3, 2002, retrieved from http://www.ncbi.nlm.nih.gov/snp/snp_ss.cgi?subsnp_id=5607016.

Database Probe [Online] NCBI Jan. 25, 2006, retrieved from http://www.ncbi.nlm.nih.gov/genome/probe/reports/probereport.cbi?uid=3131349 abstract & Database NSP [Online] NCBI Sep. 3, 2003, retrieved from http://www.ncbi.nlm.nih.gov/snp/snp_ss.cgi?subsnp_id=12674478.

Database Probe [Online] NCBI Oct. 5, 2005, retrieved from http://www.ncbi.nlm.nih.gov/genome/probe/reports/probereport.cbi?uid=1347746, the whole document & Database SNP [Online] NCBI Sep. 3, 2003, retrieved from http://www.ncbi.nlm.nih.gov/snp/snp_ss.cgi?subsnp_id=12674494.

Database Probe [Online] NCBI Jan. 24, 2006, retrieved from http://www.ncbi.nlm.nih.gov/genome/probe/reports/probereport.cgi?uid=3249825, the whole document & Database SNP [Online] NCBI Dec. 3, 2002, retrieved from http://www.ncbi.nlm.nih.gov/snp/snp_ss.cgi?subsnp_id=5606988.

Fan et al., "Molecular Diagnostics of Genetic Eyd Diseases," *Clin. Biochem.*, 39(3):231-239 (2006).

Gunderson, et al., "A Genome-Wide Scalable SNP Genotyping Assay Using Microarray Technology", *Nature Genetics*, 37(5):549-554 (2005).

Haddad et al., "The Genetics of Age-Related Macular Degeneration: A Review of Progress to Date," *Surv. Ophthalmol*, 51:316-63 (2006).

Jha et al., "The Role of Complement System in Ocular Diseases Including Uveitis and Macular Degneration," *Mol. Immunol.*, 44:3901-3908 (2007).

Maller et al., "Common Variation in Three Genes, Including a Noncoding Variant in CFH, Strongly Influences Risk of Age-Related Macular Degeneration," *Nature Genetics*, 38(9):1055-1059 (2006).

Application No. EP07750527, Supplementary European Search Report completed Sep. 22, 2009.

Application No. EP07750725, Supplementary European Search Report completed Sep. 25, 2009.

Application No. PCT/US07/061954, International Search Report of Oct. 25, 2007.

Abrera-Abeleda MA, "Variations In the complement regulatory genes factor H (CFH) and factor H related 5 (CFHR5) are associated with membranoproliferative glomerulonephritis type II (dense deposit disease)," *J. Med. Genet*, 43:582-589, 2006.

Boerhinger Mannheim, "Non-Radioactive Labeling and Detection of Nucleric Acids," *1997 Biochemical Catalog*, cover page and p. 65.

Edwards et al., "Complement Factor H Polymorphism in Age-Relaged Macular Degeneration," *Science*, 308:421-424, Apr. 15, 2005.

Hageman et al., "A common haplotype in the complement regulatory gene factor H (*HF1/CFH*) predisposes individuals to age-related macular degeneration," *PNAS*, 102:20:7227-7232, May 17, 2005.

Haines et al, "Complement Factor H Variant Increases the Risk of Age-Related Macular Degeneration," *Science* 308:419-421, Apr. 15, 2005.

Klein et al., "Complement Factor H Polymorphism in Age-Related Macular Degeneration," *Science*, 308:385-389, Apr. 15, 2005.

Reference SNP Cluster Report: rs641153 available at http://www.ncbi.nlm.nih.gov/projects/SNP, May 13, 2008.

PCT Search Report for PCT/US07/03696 of Jun. 12, 2008.

Written Opinion for PCT/US07/03696 of Jun. 12, 2008.

\* cited by examiner

SEQUENCE LISTING

```
<160> NUMBER OF SEQ ID NOS: 15

<210> SEQ ID NO 1
<211> LENGTH: 43
<212> TYPE: DNA
<213> ORGANISM: Artificial
<220> FEATURE:
<223> OTHER INFORMATION: Synthetic primer - Based on SNP ID:rs641153

<400> SEQUENCE: 1
ccactccatg gtctttggcc crgccccagg gatcctgctc tct                    43

<210> SEQ ID NO 2
<211> LENGTH: 51
<212> TYPE: DNA
<213> ORGANISM: Artificial
<220> FEATURE:
<223> OTHER INFORMATION: Synthetic primer - Based on SNP ID:rs4151667

<400> SEQUENCE: 2
atggggagca atctcagccc ccaacwctgc ctgatgccct ttatcttggg c           51

<210> SEQ ID NO 3
<211> LENGTH: 46
<212> TYPE: DNA
<213> ORGANISM: Artificial
<220> FEATURE:
<223> OTHER INFORMATION: Synthetic primer - Based on SNP ID:rs547154

<400> SEQUENCE: 3
gaggagcccg ccagaggccc gtkttgggaa cctggacaca gtgccc                 46

<210> SEQ ID NO 4
<211> LENGTH: 51
<212> TYPE: DNA
<213> ORGANISM: Artificial
<220> FEATURE:
<223> OTHER INFORMATION: Synthetic primer - Based on SNP ID:rs9332739

<400> SEQUENCE: 4
acgacaactc ccgggatatg actgasgtga tcagcagcct ggaaaatgcc a           51

<210> SEQ ID NO 5
<211> LENGTH: 51
```

```
<212> TYPE: DNA
<213> ORGANISM: Artificial
<220> FEATURE:
<223> OTHER INFORMATION: Synthetic primer - Based on SNP ID:rs1048709

<400> SEQUENCE: 5
atcgcacctg ccaagtgaat ggccgrtgga gtgggcagac agcgatctgt g        51

<210> SEQ ID NO 6
<211> LENGTH: 60
<212> TYPE: DNA
<213> ORGANISM: Artificial
<220> FEATURE:
<223> OTHER INFORMATION: Synthetic delTT polymorphism sequence

<400> SEQUENCE: 6
ccttgctatt acatactaat tcataacttt tttttcgtt ttagaaaggc cctgtggaca    60

<210> SEQ ID NO 7
<211> LENGTH: 62
<212> TYPE: DNA
<213> ORGANISM: Artificial
<220> FEATURE:
<223> OTHER INFORMATION: Synthetic delTT polymorphism sequence

<400> SEQUENCE: 7
ccttgctatt acatactaat tcataacttt tttttttcg ttttagaaag ccctgtgga    60 ca                                                                 62

<210> SEQ ID NO 8
<211> LENGTH: 51
<212> TYPE: DNA
<213> ORGANISM: Artificial
<220> FEATURE:
<223> OTHER INFORMATION: Synthetic primer - Based on SNP ID:rs1061170

<400> SEQUENCE: 8
tttggaaaat ggatataatc aaaatyatgg aagaaagttt gtacagggta a           51

<210> SEQ ID NO 9
<211> LENGTH: 764
<212> TYPE: PRT
<213> ORGANISM: Artificial
<220> FEATURE:
<223> OTHER INFORMATION: Synthetic Factor B amino acid sequence 9H and
      32R

<400> SEQUENCE: 9
```

Met Gly Ser Asn Leu Ser Pro Gln His Cys Leu Met Pro Phe Ile Leu
1               5                   10                  15

Gly Leu Leu Ser Gly Gly Val Thr Thr Thr Pro Trp Ser Leu Ala Arg
            20                  25                  30

Pro Gln Gly Ser Cys Ser Leu Glu Gly Val Glu Ile Lys Gly Gly Ser
        35                  40                  45

Phe Arg Leu Leu Gln Glu Gly Gln Ala Leu Glu Tyr Val Cys Pro Ser
    50                  55                  60

Gly Phe Tyr Pro Tyr Pro Val Gln Thr Arg Thr Cys Arg Ser Thr Gly
65                  70                  75                  80

Ser Trp Ser Thr Leu Lys Thr Gln Asp Gln Lys Thr Val Arg Lys Ala
                85                  90                  95

Glu Cys Arg Ala Ile His Cys Pro Arg Pro His Asp Phe Glu Asn Gly
            100                 105                 110

Glu Tyr Trp Pro Arg Ser Pro Tyr Tyr Asn Val Ser Asp Glu Ile Ser

```
                  115                 120                 125
Phe His Cys Tyr Asp Gly Tyr Thr Leu Arg Gly Ser Ala Asn Arg Thr
130                 135                 140

Cys Gln Val Asn Gly Arg Trp Ser Gly Gln Thr Ala Ile Cys Asp Asn
145                 150                 155                 160

Gly Ala Gly Tyr Cys Ser Asn Pro Gly Ile Pro Ile Gly Thr Arg Lys
                    165                 170                 175

Val Gly Ser Gln Tyr Arg Leu Glu Asp Ser Val Thr Tyr His Cys Ser
                180                 185                 190

Arg Gly Leu Thr Leu Arg Gly Ser Gln Arg Arg Thr Cys Gln Glu Gly
            195                 200                 205

Gly Ser Trp Ser Gly Thr Glu Pro Ser Cys Gln Asp Ser Phe Met Tyr
        210                 215                 220

Asp Thr Pro Gln Glu Val Ala Glu Ala Phe Leu Ser Ser Leu Thr Glu
225                 230                 235                 240

Thr Ile Glu Gly Val Asp Ala Glu Asp Gly His Gly Pro Gly Glu Gln
                    245                 250                 255

Gln Lys Arg Lys Ile Val Leu Asp Pro Ser Gly Ser Met Asn Ile Tyr
                260                 265                 270

Leu Val Leu Asp Gly Ser Asp Ser Ile Gly Ala Ser Asn Phe Thr Gly
            275                 280                 285

Ala Lys Lys Cys Leu Val Asn Leu Ile Glu Lys Val Ala Ser Tyr Gly
        290                 295                 300

Val Lys Pro Arg Tyr Gly Leu Val Thr Tyr Ala Thr Tyr Pro Lys Ile
305                 310                 315                 320

Trp Val Lys Val Ser Glu Ala Asp Ser Ser Asn Ala Asp Trp Val Thr
                    325                 330                 335

Lys Gln Leu Asn Glu Ile Asn Tyr Glu Asp His Lys Leu Lys Ser Gly
                340                 345                 350

Thr Asn Thr Lys Lys Ala Leu Gln Ala Val Tyr Ser Met Met Ser Trp
            355                 360                 365

Pro Asp Asp Val Pro Pro Glu Gly Trp Asn Arg Thr Arg His Val Ile
        370                 375                 380

Ile Leu Met Thr Asp Gly Leu His Asn Met Gly Gly Asp Pro Ile Thr
385                 390                 395                 400

Val Ile Asp Glu Ile Arg Asp Leu Leu Tyr Ile Gly Lys Asp Arg Lys
                    405                 410                 415

Asn Pro Arg Glu Asp Tyr Leu Asp Val Tyr Val Phe Gly Val Gly Pro
                420                 425                 430

Leu Val Asn Gln Val Asn Ile Asn Ala Leu Ala Ser Lys Lys Asp Asn
            435                 440                 445

Glu Gln His Val Phe Lys Val Lys Asp Met Glu Asn Leu Glu Asp Val
        450                 455                 460

Phe Tyr Gln Met Ile Asp Glu Ser Gln Ser Leu Ser Leu Cys Gly Met
465                 470                 475                 480

Val Trp Glu His Arg Lys Gly Thr Asp Tyr His Lys Gln Pro Trp Gln
                    485                 490                 495

Ala Lys Ile Ser Val Ile Arg Pro Ser Lys Gly His Glu Ser Cys Met
                500                 505                 510

Gly Ala Val Val Ser Glu Tyr Phe Val Leu Thr Ala Ala His Cys Phe
            515                 520                 525

Thr Val Asp Asp Lys Glu His Ser Ile Lys Val Ser Val Gly Gly Glu
        530                 535                 540
```

```
Lys Arg Asp Leu Glu Ile Glu Val Val Leu Phe His Pro Asn Tyr Asn
545                 550                 555                 560

Ile Asn Gly Lys Lys Glu Ala Gly Ile Pro Glu Phe Tyr Asp Tyr Asp
                565                 570                 575

Val Ala Leu Ile Lys Leu Lys Asn Lys Leu Lys Tyr Gly Gln Thr Ile
            580                 585                 590

Arg Pro Ile Cys Leu Pro Cys Thr Glu Gly Thr Thr Arg Ala Leu Arg
            595                 600                 605

Leu Pro Pro Thr Thr Thr Cys Gln Gln Gln Lys Glu Glu Leu Leu Pro
        610                 615                 620

Ala Gln Asp Ile Lys Ala Leu Phe Val Ser Glu Glu Lys Lys Leu
625                 630                 635                 640

Thr Arg Lys Glu Val Tyr Ile Lys Asn Gly Asp Lys Lys Gly Ser Cys
                645                 650                 655

Glu Arg Asp Ala Gln Tyr Ala Pro Gly Tyr Asp Lys Val Lys Asp Ile
                660                 665                 670

Ser Glu Val Val Thr Pro Arg Phe Leu Cys Thr Gly Gly Val Ser Pro
            675                 680                 685

Tyr Ala Asp Pro Asn Thr Cys Arg Gly Asp Ser Gly Gly Pro Leu Ile
690                 695                 700

Val His Lys Arg Ser Arg Phe Ile Gln Val Gly Val Ile Ser Trp Gly
705                 710                 715                 720

Val Val Asp Val Cys Lys Asn Gln Lys Arg Gln Lys Gln Val Pro Ala
                725                 730                 735

His Ala Arg Asp Phe His Ile Asn Leu Phe Gln Val Leu Pro Trp Leu
            740                 745                 750

Lys Glu Lys Leu Gln Asp Glu Asp Leu Gly Phe Leu
            755                 760

<210> SEQ ID NO 10
<211> LENGTH: 764
<212> TYPE: PRT
<213> ORGANISM: Artificial
<220> FEATURE:
<223> OTHER INFORMATION: Synthetic Factor B amino acid sequence 9L and
      32Q

<400> SEQUENCE: 10

Met Gly Ser Asn Leu Ser Pro Gln Leu Cys Leu Met Pro Phe Ile Leu
1               5                   10                  15

Gly Leu Leu Ser Gly Gly Val Thr Thr Thr Pro Trp Ser Leu Ala Gln
            20                  25                  30

Pro Gln Gly Ser Cys Ser Leu Glu Gly Val Glu Ile Lys Gly Gly Ser
        35                  40                  45

Phe Arg Leu Leu Gln Glu Gly Gln Ala Leu Glu Tyr Val Cys Pro Ser
50                  55                  60

Gly Phe Tyr Pro Tyr Pro Val Gln Thr Arg Thr Cys Arg Ser Thr Gly
65                  70                  75                  80

Ser Trp Ser Thr Leu Lys Thr Gln Asp Gln Lys Thr Val Arg Lys Ala
                85                  90                  95

Glu Cys Arg Ala Ile His Cys Pro Arg Pro His Asp Phe Glu Asn Gly
                100                 105                 110

Glu Tyr Trp Pro Arg Ser Pro Tyr Tyr Asn Val Ser Asp Glu Ile Ser
            115                 120                 125

Phe His Cys Tyr Asp Gly Tyr Thr Leu Arg Gly Ser Ala Asn Arg Thr
130                 135                 140
```

-continued

```
Cys Gln Val Asn Gly Arg Trp Ser Gly Gln Thr Ala Ile Cys Asp Asn
145                 150                 155                 160

Gly Ala Gly Tyr Cys Ser Asn Pro Gly Ile Pro Ile Gly Thr Arg Lys
            165                 170                 175

Val Gly Ser Gln Tyr Arg Leu Glu Asp Ser Val Thr Tyr His Cys Ser
        180                 185                 190

Arg Gly Leu Thr Leu Arg Gly Ser Gln Arg Thr Cys Gln Glu Gly
    195                 200                 205

Gly Ser Trp Ser Gly Thr Glu Pro Ser Cys Gln Asp Ser Phe Met Tyr
210                 215                 220

Asp Thr Pro Gln Glu Val Ala Glu Ala Phe Leu Ser Ser Leu Thr Glu
225                 230                 235                 240

Thr Ile Glu Gly Val Asp Ala Glu Asp Gly His Gly Pro Gly Glu Gln
                245                 250                 255

Gln Lys Arg Lys Ile Val Leu Asp Pro Ser Gly Ser Met Asn Ile Tyr
            260                 265                 270

Leu Val Leu Asp Gly Ser Asp Ser Ile Gly Ala Ser Asn Phe Thr Gly
        275                 280                 285

Ala Lys Lys Cys Leu Val Asn Leu Ile Glu Lys Val Ala Ser Tyr Gly
    290                 295                 300

Val Lys Pro Arg Tyr Gly Leu Val Thr Tyr Ala Thr Tyr Pro Lys Ile
305                 310                 315                 320

Trp Val Lys Val Ser Glu Ala Asp Ser Ser Asn Ala Asp Trp Val Thr
                325                 330                 335

Lys Gln Leu Asn Glu Ile Asn Tyr Glu Asp His Lys Leu Lys Ser Gly
            340                 345                 350

Thr Asn Thr Lys Lys Ala Leu Gln Ala Val Tyr Ser Met Met Ser Trp
        355                 360                 365

Pro Asp Asp Val Pro Pro Glu Gly Trp Asn Arg Thr Arg His Val Ile
    370                 375                 380

Ile Leu Met Thr Asp Gly Leu His Asn Met Gly Gly Asp Pro Ile Thr
385                 390                 395                 400

Val Ile Asp Glu Ile Arg Asp Leu Leu Tyr Ile Gly Lys Asp Arg Lys
                405                 410                 415

Asn Pro Arg Glu Asp Tyr Leu Asp Val Tyr Val Phe Gly Val Gly Pro
            420                 425                 430

Leu Val Asn Gln Val Asn Ile Asn Ala Leu Ala Ser Lys Lys Asp Asn
        435                 440                 445

Glu Gln His Val Phe Lys Val Lys Asp Met Glu Asn Leu Glu Asp Val
    450                 455                 460

Phe Tyr Gln Met Ile Asp Glu Ser Gln Ser Leu Ser Leu Cys Gly Met
465                 470                 475                 480

Val Trp Glu His Arg Lys Gly Thr Asp Tyr His Lys Gln Pro Trp Gln
                485                 490                 495

Ala Lys Ile Ser Val Ile Arg Pro Ser Lys Gly His Glu Ser Cys Met
            500                 505                 510

Gly Ala Val Val Ser Glu Tyr Phe Val Leu Thr Ala Ala His Cys Phe
        515                 520                 525

Thr Val Asp Asp Lys Glu His Ser Ile Lys Val Ser Val Gly Gly Glu
    530                 535                 540

Lys Arg Asp Leu Glu Ile Glu Val Val Leu Phe His Pro Asn Tyr Asn
545                 550                 555                 560

Ile Asn Gly Lys Lys Glu Ala Gly Ile Pro Glu Phe Tyr Asp Tyr Asp
                565                 570                 575
```

Val Ala Leu Ile Lys Leu Lys Asn Lys Leu Lys Tyr Gly Gln Thr Ile
            580                 585                 590

Arg Pro Ile Cys Leu Pro Cys Thr Glu Gly Thr Thr Arg Ala Leu Arg
            595                 600                 605

Leu Pro Pro Thr Thr Cys Gln Gln Gln Lys Glu Glu Leu Leu Pro
610                 615                 620

Ala Gln Asp Ile Lys Ala Leu Phe Val Ser Glu Glu Lys Leu
625                 630                 635                 640

Thr Arg Lys Glu Val Tyr Ile Lys Asn Gly Asp Lys Lys Gly Ser Cys
            645                 650                 655

Glu Arg Asp Ala Gln Tyr Ala Pro Gly Tyr Asp Lys Val Lys Asp Ile
            660                 665                 670

Ser Glu Val Val Thr Pro Arg Phe Leu Cys Thr Gly Gly Val Ser Pro
            675                 680                 685

Tyr Ala Asp Pro Asn Thr Cys Arg Gly Asp Ser Gly Gly Pro Leu Ile
            690                 695                 700

Val His Lys Arg Ser Arg Phe Ile Gln Val Gly Val Ile Ser Trp Gly
705                 710                 715                 720

Val Val Asp Val Cys Lys Asn Gln Lys Arg Gln Lys Gln Val Pro Ala
            725                 730                 735

His Ala Arg Asp Phe His Ile Asn Leu Phe Gln Val Leu Pro Trp Leu
            740                 745                 750

Lys Glu Lys Leu Gln Asp Glu Asp Leu Gly Phe Leu
            755                 760

<210> SEQ ID NO 11
<211> LENGTH: 764
<212> TYPE: PRT
<213> ORGANISM: Artificial
<220> FEATURE:
<223> OTHER INFORMATION: Synthetic Factor B amino acid sequence 9H and
      32Q

<400> SEQUENCE: 11

Met Gly Ser Asn Leu Ser Pro Gln His Cys Leu Met Pro Phe Ile Leu
1               5                   10                  15

Gly Leu Leu Ser Gly Gly Val Thr Thr Thr Pro Trp Ser Leu Ala Gln
            20                  25                  30

Pro Gln Gly Ser Cys Ser Leu Glu Gly Val Glu Ile Lys Gly Gly Ser
            35                  40                  45

Phe Arg Leu Leu Gln Glu Gly Gln Ala Leu Glu Tyr Val Cys Pro Ser
50                  55                  60

Gly Phe Tyr Pro Tyr Pro Val Gln Thr Arg Thr Cys Arg Ser Thr Gly
65                  70                  75                  80

Ser Trp Ser Thr Leu Lys Thr Gln Asp Gln Lys Thr Val Arg Lys Ala
            85                  90                  95

Glu Cys Arg Ala Ile His Cys Pro Arg Pro His Asp Phe Glu Asn Gly
            100                 105                 110

Glu Tyr Trp Pro Arg Ser Pro Tyr Tyr Asn Val Ser Asp Glu Ile Ser
            115                 120                 125

Phe His Cys Tyr Asp Gly Tyr Thr Leu Arg Gly Ser Ala Asn Arg Thr
            130                 135                 140

Cys Gln Val Asn Gly Arg Trp Ser Gly Gln Thr Ala Ile Cys Asp Asn
145                 150                 155                 160

Gly Ala Gly Tyr Cys Ser Asn Pro Gly Ile Pro Ile Gly Thr Arg Lys
            165                 170                 175

```
Val Gly Ser Gln Tyr Arg Leu Glu Asp Ser Val Thr Tyr His Cys Ser
            180                 185                 190

Arg Gly Leu Thr Leu Arg Gly Ser Gln Arg Arg Thr Cys Gln Glu Gly
            195                 200                 205

Gly Ser Trp Ser Gly Thr Glu Pro Ser Cys Gln Asp Ser Phe Met Tyr
210                 215                 220

Asp Thr Pro Gln Glu Val Ala Glu Ala Phe Leu Ser Ser Leu Thr Glu
225                 230                 235                 240

Thr Ile Glu Gly Val Asp Ala Glu Asp Gly His Gly Pro Gly Glu Gln
                245                 250                 255

Gln Lys Arg Lys Ile Val Leu Asp Pro Ser Gly Ser Met Asn Ile Tyr
            260                 265                 270

Leu Val Leu Asp Gly Ser Asp Ser Ile Gly Ala Ser Asn Phe Thr Gly
            275                 280                 285

Ala Lys Lys Cys Leu Val Asn Leu Ile Glu Lys Val Ala Ser Tyr Gly
            290                 295                 300

Val Lys Pro Arg Tyr Gly Leu Val Thr Tyr Ala Thr Tyr Pro Lys Ile
305                 310                 315                 320

Trp Val Lys Val Ser Glu Ala Asp Ser Ser Asn Ala Asp Trp Val Thr
                325                 330                 335

Lys Gln Leu Asn Glu Ile Asn Tyr Glu Asp His Lys Leu Lys Ser Gly
            340                 345                 350

Thr Asn Thr Lys Lys Ala Leu Gln Ala Val Tyr Ser Met Met Ser Trp
            355                 360                 365

Pro Asp Asp Val Pro Pro Glu Gly Trp Asn Arg Thr Arg His Val Ile
370                 375                 380

Ile Leu Met Thr Asp Gly Leu His Asn Met Gly Gly Asp Pro Ile Thr
385                 390                 395                 400

Val Ile Asp Glu Ile Arg Asp Leu Leu Tyr Ile Gly Lys Asp Arg Lys
                405                 410                 415

Asn Pro Arg Glu Asp Tyr Leu Asp Val Tyr Val Phe Gly Val Gly Pro
            420                 425                 430

Leu Val Asn Gln Val Asn Ile Asn Ala Leu Ala Ser Lys Lys Asp Asn
            435                 440                 445

Glu Gln His Val Phe Lys Val Lys Asp Met Glu Asn Leu Glu Asp Val
            450                 455                 460

Phe Tyr Gln Met Ile Asp Glu Ser Gln Ser Leu Ser Leu Cys Gly Met
465                 470                 475                 480

Val Trp Glu His Arg Lys Gly Thr Asp Tyr His Lys Gln Pro Trp Gln
                485                 490                 495

Ala Lys Ile Ser Val Ile Arg Pro Ser Lys Gly His Glu Ser Cys Met
            500                 505                 510

Gly Ala Val Val Ser Glu Tyr Phe Val Leu Thr Ala Ala His Cys Phe
            515                 520                 525

Thr Val Asp Asp Lys Glu His Ser Ile Lys Val Ser Val Gly Gly Glu
            530                 535                 540

Lys Arg Asp Leu Glu Ile Glu Val Val Leu Phe His Pro Asn Tyr Asn
545                 550                 555                 560

Ile Asn Gly Lys Lys Glu Ala Gly Ile Pro Glu Phe Tyr Asp Tyr Asp
                565                 570                 575

Val Ala Leu Ile Lys Leu Lys Asn Lys Leu Lys Tyr Gly Gln Thr Ile
            580                 585                 590

Arg Pro Ile Cys Leu Pro Cys Thr Glu Gly Thr Thr Arg Ala Leu Arg
```

```
                595                 600                 605
Leu Pro Pro Thr Thr Thr Cys Gln Gln Gln Lys Glu Glu Leu Leu Pro
            610                 615                 620

Ala Gln Asp Ile Lys Ala Leu Phe Val Ser Glu Glu Lys Lys Leu
625                 630                 635                 640

Thr Arg Lys Glu Val Tyr Ile Lys Asn Gly Asp Lys Lys Gly Ser Cys
                645                 650                 655

Glu Arg Asp Ala Gln Tyr Ala Pro Gly Tyr Asp Lys Val Lys Asp Ile
            660                 665                 670

Ser Glu Val Val Thr Pro Arg Phe Leu Cys Thr Gly Gly Val Ser Pro
                675                 680                 685

Tyr Ala Asp Pro Asn Thr Cys Arg Gly Asp Ser Gly Gly Pro Leu Ile
            690                 695                 700

Val His Lys Arg Ser Arg Phe Ile Gln Val Gly Val Ile Ser Trp Gly
705                 710                 715                 720

Val Val Asp Val Cys Lys Asn Gln Lys Arg Gln Lys Gln Val Pro Ala
                725                 730                 735

His Ala Arg Asp Phe His Ile Asn Leu Phe Gln Val Leu Pro Trp Leu
            740                 745                 750

Lys Glu Lys Leu Gln Asp Glu Asp Leu Gly Phe Leu
        755                 760

<210> SEQ ID NO 12
<211> LENGTH: 752
<212> TYPE: PRT
<213> ORGANISM: Artificial
<220> FEATURE:
<223> OTHER INFORMATION: Synthetic Complement component 2 amino acid
      sequence 318D

<400> SEQUENCE: 12

Met Gly Pro Leu Met Val Leu Phe Cys Leu Leu Phe Leu Tyr Pro Gly
1               5                   10                  15

Leu Ala Asp Ser Ala Pro Ser Cys Pro Gln Asn Val Asn Ile Ser Gly
            20                  25                  30

Gly Thr Phe Thr Leu Ser His Gly Trp Ala Pro Gly Ser Leu Leu Thr
        35                  40                  45

Tyr Ser Cys Pro Gln Gly Leu Tyr Pro Ser Pro Ala Ser Arg Leu Cys
50                  55                  60

Lys Ser Ser Gly Gln Trp Gln Thr Pro Gly Ala Thr Arg Ser Leu Ser
65                  70                  75                  80

Lys Ala Val Cys Lys Pro Val Arg Cys Pro Ala Pro Val Ser Phe Glu
                85                  90                  95

Asn Gly Ile Tyr Thr Pro Arg Leu Gly Ser Tyr Pro Val Gly Gly Asn
            100                 105                 110

Val Ser Phe Glu Cys Glu Asp Gly Phe Ile Leu Arg Gly Ser Pro Val
        115                 120                 125

Arg Gln Cys Arg Pro Asn Gly Met Trp Asp Gly Glu Thr Ala Val Cys
130                 135                 140

Asp Asn Gly Ala Gly His Cys Pro Asn Pro Gly Ile Ser Leu Gly Ala
145                 150                 155                 160

Val Arg Thr Gly Phe Arg Phe Gly His Gly Asp Lys Val Arg Tyr Arg
                165                 170                 175

Cys Ser Ser Asn Leu Val Leu Thr Gly Ser Ser Glu Arg Glu Cys Gln
            180                 185                 190

Gly Asn Gly Val Trp Ser Gly Thr Glu Pro Ile Cys Arg Gln Pro Tyr
```

-continued

```
                195                 200                 205
Ser Tyr Asp Phe Pro Glu Asp Val Ala Pro Ala Leu Gly Thr Ser Phe
210                 215                 220

Ser His Met Leu Gly Ala Thr Asn Pro Thr Gln Lys Thr Lys Glu Ser
225                 230                 235                 240

Leu Gly Arg Lys Ile Gln Ile Gln Arg Ser Gly His Leu Asn Leu Tyr
                245                 250                 255

Leu Leu Leu Asp Cys Ser Gln Ser Val Ser Glu Asn Asp Phe Leu Ile
                260                 265                 270

Phe Lys Glu Ser Ala Ser Leu Met Val Asp Arg Ile Phe Ser Phe Glu
                275                 280                 285

Ile Asn Val Ser Val Ala Ile Ile Thr Phe Ala Ser Glu Pro Lys Val
            290                 295                 300

Leu Met Ser Val Leu Asn Asp Asn Ser Arg Asp Met Thr Asp Val Ile
305                 310                 315                 320

Ser Ser Leu Glu Asn Ala Asn Tyr Lys Asp His Glu Asn Gly Thr Gly
                325                 330                 335

Thr Asn Thr Tyr Ala Ala Leu Asn Ser Val Tyr Leu Met Met Asn Asn
                340                 345                 350

Gln Met Arg Leu Leu Gly Met Glu Thr Met Ala Trp Gln Glu Ile Arg
                355                 360                 365

His Ala Ile Ile Leu Leu Thr Asp Gly Lys Ser Asn Met Gly Gly Ser
                370                 375                 380

Pro Lys Thr Ala Val Asp His Ile Arg Glu Ile Leu Asn Ile Asn Gln
385                 390                 395                 400

Lys Arg Asn Asp Tyr Leu Asp Ile Tyr Ala Ile Gly Val Gly Lys Leu
                405                 410                 415

Asp Val Asp Trp Arg Glu Leu Asn Glu Leu Gly Ser Lys Lys Asp Gly
                420                 425                 430

Glu Arg His Ala Phe Ile Leu Gln Asp Thr Lys Ala Leu His Gln Val
                435                 440                 445

Phe Glu His Met Leu Asp Val Ser Lys Leu Thr Asp Thr Ile Cys Gly
                450                 455                 460

Val Gly Asn Met Ser Ala Asn Ala Ser Asp Gln Glu Arg Thr Pro Trp
465                 470                 475                 480

His Val Thr Ile Lys Pro Lys Ser Gln Glu Thr Cys Arg Gly Ala Leu
                485                 490                 495

Ile Ser Asp Gln Trp Val Leu Thr Ala Ala His Cys Phe Arg Asp Gly
                500                 505                 510

Asn Asp His Ser Leu Trp Arg Val Asn Val Gly Asp Pro Lys Ser Gln
                515                 520                 525

Trp Gly Lys Glu Phe Leu Ile Glu Lys Ala Val Ile Ser Pro Gly Phe
                530                 535                 540

Asp Val Phe Ala Lys Lys Asn Gln Gly Ile Leu Glu Phe Tyr Gly Asp
545                 550                 555                 560

Asp Ile Ala Leu Leu Lys Leu Ala Gln Lys Val Lys Met Ser Thr His
                565                 570                 575

Ala Arg Pro Ile Cys Leu Pro Cys Thr Met Glu Ala Asn Leu Ala Leu
                580                 585                 590

Arg Arg Pro Gln Gly Ser Thr Cys Arg Asp His Glu Asn Glu Leu Leu
                595                 600                 605

Asn Lys Gln Ser Val Pro Ala His Phe Val Ala Leu Asn Gly Ser Lys
                610                 615                 620
```

```
Leu Asn Ile Asn Leu Lys Met Gly Val Glu Trp Thr Ser Cys Ala Glu
625                 630                 635                 640

Val Val Ser Gln Glu Lys Thr Met Phe Pro Asn Leu Thr Asp Val Arg
                645                 650                 655

Glu Val Val Thr Asp Gln Phe Leu Cys Ser Gly Thr Gln Glu Asp Glu
                660                 665                 670

Ser Pro Cys Lys Gly Glu Ser Gly Gly Ala Val Phe Leu Glu Arg Arg
            675                 680                 685

Phe Arg Phe Gln Val Gly Leu Val Ser Trp Gly Leu Tyr Asn Pro
    690                 695                 700

Cys Leu Gly Ser Ala Asp Lys Asn Ser Arg Lys Arg Ala Pro Arg Ser
705                 710                 715                 720

Lys Val Pro Pro Arg Asp Phe His Ile Asn Leu Phe Arg Met Gln
                725                 730                 735

Pro Trp Leu Arg Gln His Leu Gly Asp Val Leu Asn Phe Leu Pro Leu
                740                 745                 750

<210> SEQ ID NO 13
<211> LENGTH: 9
<212> TYPE: PRT
<213> ORGANISM: Artificial
<220> FEATURE:
<223> OTHER INFORMATION: Synthetic 9 Factor B amino acid sequence 32Q

<400> SEQUENCE: 13

Trp Ser Leu Ala Gln Pro Gln Gly Ser
1               5

<210> SEQ ID NO 14
<211> LENGTH: 9
<212> TYPE: PRT
<213> ORGANISM: Artificial
<220> FEATURE:
<223> OTHER INFORMATION: Synthetic 9 Factor B amino acid sequence 9H

<400> SEQUENCE: 14

Leu Ser Pro Gln His Cys Leu Met Pro
1               5

<210> SEQ ID NO 15
<211> LENGTH: 7
<212> TYPE: PRT
<213> ORGANISM: Artificial
<220> FEATURE:
<223> OTHER INFORMATION: Synthetic 7 Complement component 2 amino acid
      sequence 318D

<400> SEQUENCE: 15

Asp Met Thr Asp Val Ile Ser
1               5
```

VARIANTS IN COMPLEMENT REGULATORY GENES PREDICT AGE-RELATED MACULAR DEGENERATION

CROSS-REFERENCE TO RELATED APPLICATIONS

This application claims benefit of U.S. provisional application Nos. 60/772,989 and 60/772,688, both filed Feb. 13, 2006, the entire contents of which are incorporated herein by reference.

The Sequence Listing written in file 020618002420US_SeqList.txt is 29,203 bytes and was created on Feb. 21, 2008 for application Ser. No. 11/706,074, Allikmets et al., VARIANTS IN COMPLEMENT REGULATORY GENES PREDICT AGE-RELATED MACULAR DEGENERATION. The information contained in this file is hereby incorporated by reference.

ACKNOWLEDGMENT OF GOVERNMENT SUPPORT

This invention was made in part by an agency of the US government with United States government support pursuant to Grant Nos. EY13435 (RA) and EY11515 (GSH) from the National Institutes of Health and with the assistance of Federal funds from the National Cancer Institute, National Institutes of Health, under Contract No. NO1-CO-124000. The United States government has certain rights in the invention.

FIELD

This application relates to methods of predicting an individual's genetic susceptibility to age-related macular degeneration.

BACKGROUND

Age-related macular degeneration (AMD) is a degenerative eye disease that affects the macula, which is a photoreceptor-rich area of the central retina that provides detailed vision. AMD results in a sudden worsening of central vision that usually only leaves peripheral vision intact. AMD is the most common form of irreversible blindness in developed countries. The disease typically presents with a decrease in central vision in one eye, followed within months or years by a similar loss of central vision in the other eye. Clinical signs of the disease include the presence of deposits (drusen) in the macula.

Despite being a major public health burden, the etiology and pathogenesis of AMD are still poorly understood. Numerous studies have implicated inflammation in the pathobiology of AMD (Anderson et al. (2002) *Am. J. Ophthalmol.* 134:411-31; Hageman et al. (2001) *Prog. Retin. Eye Res.* 20:705-32; Mullins et al. (2000) *Faseb J.* 14:835-46; Johnson et al. (2001) *Exp. Eye Res.* 73:887-96; Crabb et al. (2002) *Proc. Natl. Acad. Sci. U.S.A.* 99:14682-7; Bok, D. (2005) *Proc. Natl. Acad. Sci. U.S.A.* 102:7053-4). Dysfunction of the complement pathway may induce significant bystander damage to macular cells, leading to atrophy, degeneration, and the elaboration of choroidal neovascular membranes, similar to damage that occurs in other complement-mediated disease processes (Hageman et al. (2005) *Proc. Natl. Acad. Sci. U.S.A.* 102:7227-32; Morgan and Walport (1991) *Immunol. Today* 12:301-6; Kinoshita (1991) *Immunol. Today* 12:291-5; Holers and Thurman (2004) *Mol. Immunol.* 41: 147-52). There may be a strong genetic contribution to the disease. For example, variants in the FBLN6, ABCA4, and APOE genes have been implicated as risk factors. Recently, it was discovered that a variant in the complement factor H gene (CFH), which encodes a major inhibitor of the alternative complement pathway, is associated with increased risk of developing AMD (Haines et al. (2005) *Science* 308:419-21; Klein et al. (2005) *Science* 308:385-9; Edwards et al. (2005) *Science* 308:421-4; Hageman et al. (2005) *Proc. Natl. Acad. Sci. U.S.A.* 102:7227-32).

Due to the prevalence of the disease and the limited treatment available, methods for identifying subjects at risk for developing AMD are needed.

SUMMARY

Polymorphisms and genotypes that are protective for age-related macular degeneration (AMD) have been identified. Methods are provided for identifying a subject at increased risk for developing AMD. These methods include, but are not limited to, analyzing the subject's factor B (BF) and/or complement component 2 (C2) genes, and determining whether the subject has at least one protective polymorphism. Examples of such protective polymorphisms include (a) R32Q in BF (rs641153); (b) L9H in BF (rs4151667); (c) IVS 10 in C2 (rs547154); and (d) E318D in C2 (rs9332739). Alternatively, the method may be implemented by detecting a protein variant in the subject. If the subject does not have at least one protective polymorphism, the subject is at increased risk for developing AMD. In one embodiment of this aspect, further analysis of the subject's CFH gene is performed. In some embodiments, the subject's genotype may be analyzed at the CFH locus to determine if the subject has at least one protective genotype. In one embodiment the subject's genotype may be analyzed at either the BF or C2 locus and at the CFH locus to determine if the subject has at least one protective genotype. As disclosed hereafter, in several instances, it will be informative to learn whether the subject is homozygous or heterozygous for the polymorphism.

Examples of protective genotypes include: (a) heterozygous for the R32Q polymorphism in BF (rs641153); (b) heterozygous for the L9H polymorphism in BF (rs4151667); (c) heterozygous for the IVS 10 polymorphism in C2 (rs547154); (d) heterozygous for the E318D polymorphism in C2 (rs9332739); (e) homozygous for the delTT polymorphism in CFH; (f) homozygous for the RI 50R polymorphism in BF (rs1048709); and (g) homozygous for Y402 in CFH. If the subject does not have at least one protective genotype, the subject is at increased risk for developing AMD.

The invention provides a method for assessing the risk of development of, or likely progression of, macular degeneration or other complement mediated disease in a human subject. Underlying the methods are discoveries made through genetic association studies relating certain genetic features to risk or protective phenotypes of complement related disease, in this case, age related macular degeneration. The methods of the invention include the steps of obtaining a biological sample from a human subject, and analyzing the sample by any validated technique known in the art to determine whether the subject carries one or more of:

A or G at rs641153 of the BF gene, which translates to an R or Q at position 32 of the human BF protein;

A or T at rs4151667 of the BF gene, which translates to an L or H at position 9 of the human BF protein;

G or T at rs547154 of the C2 gene, which is in intron 10;

C or G at rs9332739 rs9332379 of the C2 gene, which translates to an E or D at position 318 of the human C2 protein;

C or G at of the C2 gene, which translates to an E or D at position 318 of the human C2 protein;

A or G at rs1048709 of the BF gene, which translates to a Rat position 150;

delTT in the CFH gene; and

C or T at rs1061170 of the CFH gene, which translates to a Y or H at position 402 of the human CFH protein.

In certain embodiments the sample is analyzed to determine whether the subject carries one or more of:

A or G at rs641153 of the BF gene, which translates to an R or Q at position 32 of the human BF protein;

A or T at rs4151667 of the BF gene, which translates to an L or H at position 9 of the human BF protein;

G or T at rs547154 of the C2 gene, which is in intron 10; and,

C or G at rs9332739 rs9332379 of the C2 gene, which translates to an E or D at position 318 of the human C2 protein.

In some embodiments, the sample is an accessible body fluid, such as blood or a blood component, or urine. When assessment is done at the DNA or mRNA level, cellular material will be required to enable detection of a genotype from a cell of the subject.

In some embodiments, the subject may have been diagnosed with a condition including AMD, early AMD, choroidal neovascularization (CNV), or geographic atrophy (GA). In one embodiment, the subject has symptoms of disease, e.g., early stage macular degeneration symptoms such as the development of drusen. Some of the subjects may present with drusen development. The subject may be asymptomatic of macular degeneration or other complement related disease, in which case, the analysis essentially provides a screening procedure which can be done on the population generally or on some segment that is thought to be at increased risk, such as individuals with a family history of complement related disease. Yet additional subjects may be at high risk for acquiring AMD. In one embodiment the subject has the Y402H SNP.

Thus, in another aspect, the invention provides a kit for assessing the risk of development of, or likely progression of, macular degeneration or other complement mediated disease in a human subject. The kit includes a collection of reagents for detecting in a sample from the subject one or more, preferably two or more of the polymorphisms or allelic variants listed above. It may comprise oligonucleotides, typically labeled oligonucleotides, designed to detect a variant using any number of methods known to the art. The kit may include, for example, PCR primers for amplifying a target polynucleotide sequence when the target is a polymorphism, or a specific binding protein, e.g., a monoclonal antibody, that recognizes and binds specifically to an allelic variant of a target protein as a basis for obtaining the relevant genetic/proteomic information from the sample. In a preferred embodiment, the kit contains oligonucleotides immobilized on a solid support.

Depending on the format, the components in a kit for identifying a subject at increased risk for developing age-related macular degeneration (AMD) will include one or more reagents for detecting at least one protective polymorphism in the subject. Such reagents allow detection of at least one protective polymorphism including: (a) R32Q in BF (rs641153); (b) L9H in BF (rs4151667); (c) IVS 10 in C2 (rs547154); and (d) E318D in C2 (rs9332739). The reagents in such kits may include one or more oligonucleotides that detect the protective polymorphism. Other kit components can include one or more reagents for amplifying a target sequence, where the target sequence encompasses one or more of the protective polymorphisms. In some versions of the kit, the one or more oligonucleotides are immobilized on a solid support.

In a related aspect the invention provides microarrays for identifying a subject at increased risk for developing AMD. In further aspects, this invention provides microarrays containing oligonucleotide probes capable of hybridizing under stringent conditions to one or more nucleic acid molecules having a protective polymorphism. Examples of such protective polymorphisms include: (a) R32Q in BF (rs641153); (b) L9H in BF (rs4151667); (c) IVS 10 in C2 (rs547154); and (d) E318D in C2 (rs9332739). Such microarrays can further contain oligonucleotide probes capable of hybridizing under stringent conditions to one or more additional nucleic acid molecules having a polymorphism that includes, for example, (a) the delTT polymorphism in CFH; (b) the R150R polymorphism in BF; and (c) the Y402H polymorphism in CFH.

The foregoing and other features and advantages of the disclosure will become more apparent from the following detailed description of several embodiments.

SEQUENCES

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. All sequence database accession numbers referenced herein are understood to refer to the version of the sequence identified by that accession number as it was available on the designated date. In the accompanying sequence listing:

SEQ ID NO: 1 is based on the SNP with refSNP ID:rs641153 as available through NCBI on Jan. 30, 2006 (revised Jan. 5, 2006). This SNP has an A or a G at nucleotide position 22, generating an R32Q variant (glutamine instead of arginine at amino acid position 32) in the BF gene. The sequence provided for R32Q is (SEQ ID NO: 1)
CCACTCCATGGTCTTTGGCCCRGCCCCAGGGATCCTGCTCTCT where R = A or G.

SEQ ID NO:2 shows the SNP with refSNP ID:rs4151667 as available through NCBI on Jan. 30, 2006 (revised Jan. 5, 2006). This SNP has an A or a T at nucleotide position 26, generating an L9H variant (histidine instead of leucine at amino acid position 9) in the BF gene. The sequence provided for rs4151667 is (SEQ ID NO: 2)
ATGGGGAGCAATCTCAGCCCCCAACRCTGCCTGATGCCCTTTATCTT GGGC where R = A or T.

SEQ ID NO: 3 is based on the SNP with refSNP ID:rs547154 as available through NCBI on Jan. 30, 2006 (revised Jan. 5, 2006). This SNP has a G or a T at nucleotide position 23 in intron 10 of the C2 gene. The sequence provided for rs547154 is

```
                                               (SEQ ID NO: 3)
GAGGAGCCCGCCAGAGGCCCGTRTTGGGAACCTGGACACAGTGCCC
``` where R is G or T.

SEQ ID NO:4 shows the SNP with refSNP ID:rs9332739 as available through NCBI on Jan. 30, 2006 (revised Jan. 5, 2006). This SNP has a C or a G at nucleotide position 26, generating an E318D variant (aspartic acid instead of glutamic acid at amino acid position 318) in the C2 gene. The sequence provided for rs9332739 is

```
                                               (SEQ ID NO: 4)
ACGACAACTCCCGGGATATGACTGARGTGATCAGCAGCCTGGAAAAT
GCCA
```
where R is C or G.

SEQ ID NO:5 shows the SNP with refSNP ID:rs1048709 as available through NCBI on Jan. 30, 2006 (revised Jan. 5, 2006). This SNP has an A or a G at nucleotide position 26 in the BF gene. This SNP does not cause an amino acid change at position 150 (R150R). The sequence provided for rs048709 is

```
                                               (SEQ ID NO: 5)
ATCGCACCTGCCAAGTGAATGGCCGRTGGAGTGGGCAGACAGCGATC
TGTG
```
where R is A or G.

SEQ ID NOS: 6 and 7 show the delTT polymorphism sequences. The delTT polymorphism is a 2 bp insertion/deletion polymorphism. The sequences are as follows:

```
                                               (SEQ ID NO: 6)
CCTTGCTATTACATACTAATTCATAACTTTTTTTTCGTTTTAGAAAGGC
CCTGTGGACA;
and
                                               (SEQ ID NO: 7)
CCTTGCTATTACATACTAATTCATAACTTTTTTTTTTCGTTTTAGAAAG
GCCCTGTGGACA.
```

SEQ ID NO:8 shows the SNP with refSNP ID:rs1061170 as available through NCBI on Jan. 30, 2006 (revised Jan. 5, 2006). This SNP has a C or a T at nucleotide 1277 in exon 9 (nucleotide 26 in the below sequence), generating a Y402H variant (histidine instead of tyrosine at amino acid position 402) in the CFH gene. The sequence provided for rs1061170 is

```
                                               (SEQ ID NO: 8)
TTTGGAAAATGGATATAATCAAAATRATGGAAGAAAGTTTGTACAGGGT
AA
```
where R is C or T.

SEQ ID NO: 9 shows the entire BF amino acid sequence with 9H & 32R)

```
                                               (SEQ ID NO: 9)
mgsnlspqhc lmpfilglls ggvtttpwsl arpqgscsle
gveikggsfr llqegqaley vcpsgfypyp vqtrtcrstg
swstlktqdq ktvrkaecra ihcprphdfe ngeywprspy
ynvsdeisfh cydgytlrgs anrtcqvngr wsgqtaicdn
gagycsnpgi pigtrkvgsq yrledsvtyh csrgltlrgs
qrrtcqeggs wsgtepscqd sfmydtpqev aeaflsslte
tiegvdaedg hgpgeqqkr↓k ivldpsgsmn iylvldgsds
igasnftgak kclvnliekv asygvkpryg lvtyatypki
wvkvseadss nadwvtkqln einyedhklk sgtntkkalq
avysmmswpd dvppegwnrt rhviilmtdg lhnmggdpit
videirdlly igkdrknpre dyldvyvfgv gplvnqvnin
alaskkdneq hvfkvkdmen ledvfyqmid esqslslcgm
vwehrkgtdy hkqpwqakis virpskghes cmgavvseyf
vltaahcftv ddkehsikvs vggekrdlei evvlfhpnyn
ingkkeagip efydydvali klknklkygq tirpiclpct
egttralrlp ptttcqqqke ellpaqdika lfvseeekkl
trkevyikng dkkgscerda qyapgydkvk disevvtprf
lctggvspya dpntcrgdsg gplivhkrsr fiqvgviswg
vvdvcknqkr qkqvpahard fhinlfqvlp wlkeklqded lgfl
```

SEQ ID NO: 10 shows the entire BF amino acid sequence with 9L & 32Q:

```
                                               (SEQ ID NO: 10)
mgsnlspqlc lmpfilglls ggvtttpwsl aqpqgscsle
gveikggsfr llqegqaley vcpsgfypyp vqtrtcrstg
swstlktqdq ktvrkaecra ihcprphdfe ngeywprspy
ynvsdeisfh cydgytlrgs anrtcqvngr wsgqtaicdn
gagycsnpgi pigtrkvgsq yrledsvtyh csrgltlrgs
qrrtcqeggs wsgtepscqd sfmydtpqev aeaflsslte
tiegvdaedg hgpgeqqkr↓k ivldpsgsmn iylvldgsds
igasnftgak kclvnliekv asygvkpryg lvtyatypki
wvkvseadss nadwvtkqln einyedhklk sqtntkkalq
avysmmswpd dvppegwnrt rhviilmtdg lhnmggdpit
videirdlly igkdrknpre dyldvyvfgv gplvnqvnin
alaskkdneq hvfkvkdmen ledvfyqmid esqslslcgm
vwehrkgtdy hkqpwqakis virpskghes cmgavvseyf
vltaahcftv ddkehsikvs vggekrdlei evvlfhpnyn
ingkkeagip efydydvali klknklkygq tirpiclpct
egttralrlp ptttcqqqke ellpaqdika lfvseeekkl
trkevyikng dkkgscerda qyapgydkvk disevvtprf
lctggvspya dpntcrgdsg gplivhkrsr fiqvgviswg
vvdvcknqkr qkqvpahard fhinlfqvlp wlkeklqded lgfl
```

SEQ ID NO: 11 shows the entire BF amino acid sequence with 9H & 32Q:

(SEQ ID NO: 11)
```
mgsnlspqhc lmpfilglls ggvtttpwsl aqpqgscsle gveikggsfr llqegqaley vcpsgfypyp vqtrtcrstg swstlktqdq ktvrkaecra ihcprphdfe ngeywprspy ynvsdeisfh cydgytlrgs anrtcqvngr wsgqtaicdn gagycsnpgi pigtrkvgsq yrledsvtyh csrgltlrgs qrrtcqeggs wsgtepscqd sfmydtpqev aeaflsslte tiegvdaedg hgpgeqqkr↓k ivldpsgsmn iylvldgsds igasnftgak kclvnliekv asygvkpryg lvtyatypki wvkvseadss nadwvtkqln einyedhklk sgtntkkalq avysmmswpd dvppegwnrt rhviilmtdg lhnmggdpit videirdlly igkdrknpre dyldvyvfgv gplvnqvnin alaskkdneq hvfkvkdmen ledvfyqmid esqslslcgm vwehrkgtdy hkqpwqakis virpskghes cmgavvseyf vltaahcftv ddkehsikvs vggekrdlei evvlfhpnyn ingkkeagip efydydvali klknklkygq tirpiclpct egttralrlp ptttcqqqke ellpaqdika lfvseeekkl trkevyikng dkkgscerda qyapgydkvk disevvtprf lctggvspya dpntcrgdsg gplivhkrsr fiqvgviswg vvdvcknqkr qkqvpahard fhinlfqvlp wlkeklqded lgfl
```

SEQ ID NO: 12 shows the entire C2 amino acid sequence with 318D:

(SEQ ID NO: 12)
```
mgplmvlfcl lflypglads apscpqnvni sggtftlshg wapgslltys cpqglypspa srlckssgqw qtpgatrsls kavckpvrcp apvsfengiy tprlgsypvg gnvsfecedg filrgspvrq crpngmwdge tavcdngagh cpnpgislga vrtgfrfghg dkvryrcssn lvltgssere cqgngvwsgt epicrqpysy dfpedvapal gtsfshmlga tnptqktkes lgrkiqiqrs ghlnlyllld csqsvsendf lifkesaslm vdrifsfein vsvaiitfas epkvlmsvln dnsrdmtdvi sslenanykd hengtgtnty aalnsvylmm nnqmrllgme tmawqeirha iilltdgksn mggspktavd hireilninq krndyldiya igvgkldvdw relnelgskk dgerhafilq dtkalhqvfe hmldvskltd ticgvgnmsa nasdqertpw hvtikpksqe tcrgalisdq wvltaahcfr dgndhslwrv nvgdpksqwg kefliekavi spgfdvfakk nqgilefygd diallklaqk vkmstharpi clpctmeanl alrrpqgstc rdhenellnk qsvpahfval ngsklninlk mgvewtscae
```
-continued
```
vvsqektmfp nltdvrevvt dqflcsgtqe despckgesg gavflerrfr ffqvglvswg lynpclgsad knsrkraprs kvppprdfhi nlfrmqpwlr qhlgdvlnfl pl
```

SEQ ID NO: 13 shows the 9 BF amino acid sequence with 32Q: wslaqpqgs (SEQ ID NO: 13).

SEQ ID NO:14 shows the 9 BF amino acid sequence with 9H: lspqhclmp (SEQ ID NO:14).

SEQ ID NO:15 shows the 7 C2 amino acid sequence with 318D: dmtdvis (SEQ ID NO: 15).

DETAILED DESCRIPTION

Figure 1:
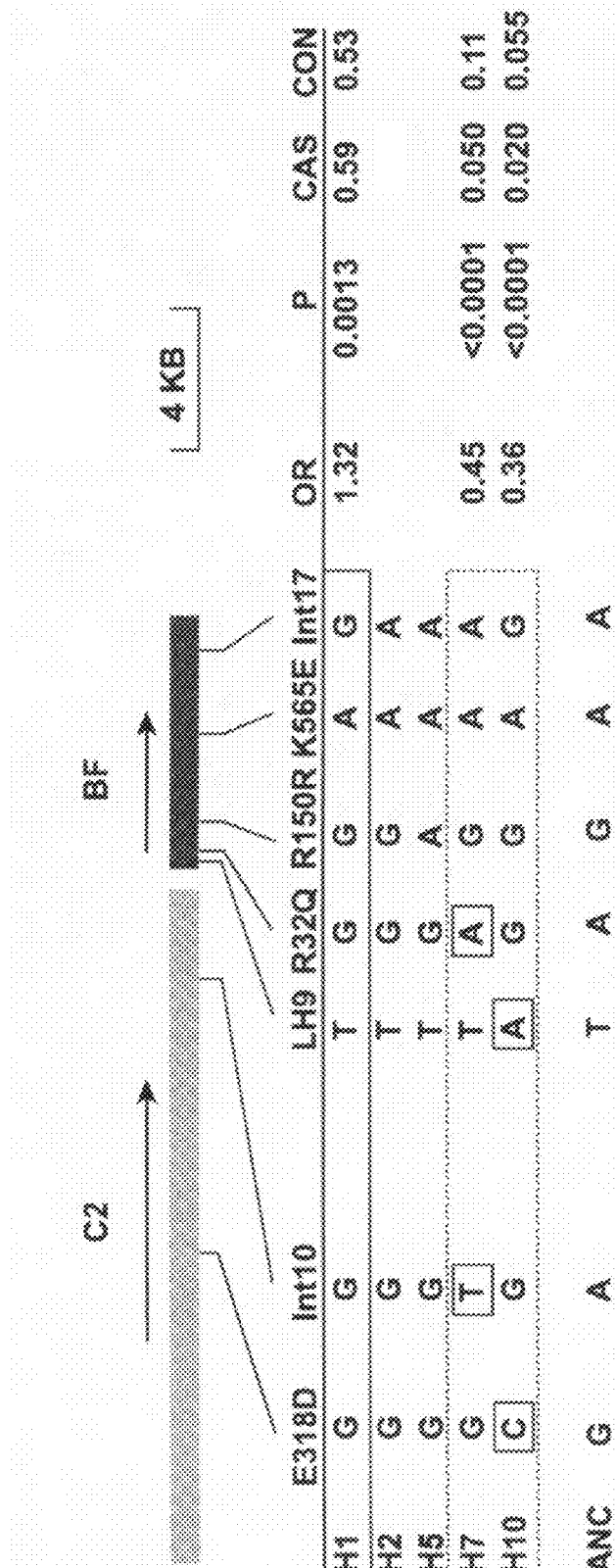
FIG. 1 is a diagram and haplotype analysis of the SNPs in BF and C2. The SNPs used in the study are shown along with the predicted haplotypes, odds ratios (OR), P values (P) and frequencies in the combined cases (CAS) and controls (CON). The 95% confidence interval for H7 is (0.33-0.61) and for H10 is (0.23-0.56). The ancestral (chimpanzee) haplotype is designated as Anc. Examples of haplotype H2 (NCBI Accession No. AL662849, as available on Feb. 8, 2006), H5 (NCBI Accession No. AL645922 and NCBI Accession No. NG_004658, as available on Feb. 8, 2006) and H7 (NCBI Accession No. NG_000013, as available on Feb. 8, 2006) have been sequenced and no additional non-synonymous variants in either the C2 or BF genes are present (Stewart et al. (2004) *Genome Res.* 14:1176-87).

Provided herein are sequence polymorphisms that were discovered to confer a protective effect against age-related macular degeneration (AMD). These polymorphisms include those found in the factor B (BF) and complement component 2 (C2) genes. Protective polymorphisms also include the delTT polymorphism in the CFH gene. Identifying subjects with these polymorphisms, as well as subjects with the recently discovered risk haplotype (Y402H in the complement factor H (CFH) gene), will aid in diagnosing those subjects at genetic risk for AMD.

Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "including a nucleic acid" includes single or plural nucleic acids and is considered equivalent to the phrase "including at least one nucleic acid." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. For example, the phrase "mutations or polymorphisms" or "one or more mutations or polymorphisms" means a mutation, a polymorphism, or combinations thereof, wherein "a" can refer to more than one.

Although methods and materials similar or equivalent to those described herein can be used in the practice or testing of the present disclosure, suitable methods and materials are described below. The materials, methods, and examples are illustrative only and not intended to be limiting.

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Age-related macular degeneration: A medical condition wherein the light sensing cells in the macula malfunction and over time cease to work. In macular degeneration the final form or the disease results in missing or blurred vision in the central, reading part of vision. The outer, peripheral part of the vision remains intact. AMD is further divided into a "dry," or nonexudative, form and a "wet," or exudative, form. Eighty five to ninety percent of cases are categorized as "dry" macular degeneration where fatty tissue, known as drusen, will slowly build up behind the retina. The classic lesion in dry macular degeneration is geographic atrophy. Ten to fifteen percent of cases involve the growth of abnormal blood vessels under the retina. These cases are called "wet" macular degeneration due to the leakage of blood and other fluid from behind the retina into the eye. Wet macular degeneration usually begins as the dry form. If allowed to continue without treatment it usually completely destroys the macular structure and function. Choroidal neovascularization is the development of abnormal blood vessels beneath the retinal pigment epithelium (RPE) layer of the retina.

Medical, photodynamic, laser photocoagulation and laser treatment of wet macular degeneration are available. Risk factors for AMD include aging, smoking, family history, exposure to sunlight especially blue light, hypertension, cardiovascular risk factors such as high cholesterol and obesity, high fat intake, oxidative stress, and race.

AMD is an example of a disease characterized by alternative complement cascade disregulation, which also includes membrane proliferative glomerulonephritis (MPGN) and a predisposition to develop aortic aneurism. Methods described herein for detection or increased risk of developing AMD may also be used to detect increased risk for other diseases characterized by alternative complement cascade disregulation (e.g., MPGN).

Allele: Any one of a number of viable DNA codings of the same gene (sometimes the term refers to a non-gene sequence) occupying a given locus (position) on a chromosome. An individual's genotype for that gene will be the set of alleles it happens to possess. In an organism which has two copies of each of its chromosomes (a diploid organism), two alleles make up the individual's genotype. In a diploid organism, when the two copies of the gene are identical—that is, have the same allele—they are said to be homozygous for that gene. A diploid organism which has two different alleles of the gene is said to be heterozygous.

As used herein, the process of "detecting alleles" may be referred to as "genotyping, determining or identifying an allele or polymorphism," or any similar phrase. The allele actually detected will be manifest in the genomic DNA of a subject, but may also be detectable from RNA or protein sequences transcribed or translated from this region.

Amplification: The use of a technique that increases the number of copies of a nucleic acid molecule in a sample. An example of in vitro amplification is the polymerase chain reaction (PCR), in which a biological sample obtained from a subject is contacted with a pair of oligonucleotide primers, under conditions that allow for hybridization of the primers to a nucleic acid molecule in the sample. The primers are extended under suitable conditions, dissociated from the template, and then re-annealed, extended, and dissociated to amplify the number of copies of the nucleic acid molecule. The product of amplification can be characterized by such techniques as electrophoresis, restriction endonuclease cleavage patterns, oligonucleotide hybridization or ligation, and/or nucleic acid sequencing.

Other examples of amplification methods include strand displacement amplification, as disclosed in U.S. Pat. No. 5,744,311; transcription-free isothermal amplification, as disclosed in U.S. Pat. No. 6,033,881; repair chain reaction amplification, as disclosed in PCT Publication No. WO 90/01069; ligase chain reaction amplification, as disclosed in EP-A-320,308; gap filling ligase chain reaction amplification, as disclosed in U.S. Pat. No. 5,427,930; and NASBA™ RNA transcription-free amplification, as disclosed in U.S. Pat. No. 6,025,134. An amplification method can be modified, including for example by additional steps or coupling the amplification with another protocol.

Array: An arrangement of molecules, particularly biological macromolecules (such as polypeptides or nucleic acids) or cell or tissue samples, in addressable locations on or in a substrate. A "microarray" is an array that is miniaturized so as to require or be aided by microscopic examination for evaluation or analysis. These arrays are sometimes called DNA chips, or—generally—biochips; though more formally they are referred to as microarrays, and the process of testing the gene patterns of an individual is sometimes called microarray profiling. DNA array fabrication chemistry and structure is varied, typically made up of 400,000 different features, each holding DNA from a different human gene, but some employing a solid-state chemistry to pattern as many as 780,000 individual features.

The array of molecules ("features") makes it possible to carry out a very large number of analyses on a sample at one time. In certain example arrays, one or more molecules (such as an oligonucleotide probe) will occur on the array a plurality of times (such as twice), for instance to provide internal controls. The number of addressable locations on the array can vary, for example from a few (such as three) to at least 50, at least 100, at least 200, at least 250, at least 300, at least 500, at least 600, at least 1000, at least 10,000, or more. In particular examples, an array includes nucleic acid molecules, such as oligonucleotide sequences that are at least 15 nucleotides in length, such as about 15-40 nucleotides in length, such as at least 18 nucleotides in length, at least 21 nucleotides in length, or even at least 25 nucleotides in length. In one example, the molecule includes oligonucleotides attached to the array via their 5'- or 3'-end.

Within an array, each arrayed sample is addressable, in that its location can be reliably and consistently determined within the at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Also contemplated herein are protein-based arrays, where the probe molecules are or include proteins, or where the target molecules are or include proteins, and arrays including nucleic acids to which proteins/peptides are bound, or vice versa.

Binding or stable binding: An association between two substances or molecules, such as the hybridization of one nucleic acid molecule to another (or itself) and the association of an antibody with a peptide. An oligonucleotide molecule binds or stably binds to a target nucleic acid molecule if a sufficient amount of the oligonucleotide molecule forms base pairs or is hybridized to its target nucleic acid molecule, to permit detection of that binding. Binding can be detected by any procedure known to one skilled in the art, such as by physical or functional properties of the target:oligonucleotide complex. For example, binding can be detected functionally by determining whether binding has an observable effect upon a biosynthetic process such as expression of a gene, DNA replication, transcription, translation, and the like.

Physical methods of detecting the binding of complementary strands of nucleic acid molecules, include but are not limited to, such methods as DNase I or chemical footprinting, gel shift and affinity cleavage assays, Northern blotting, dot blotting and light absorption detection procedures. For example, one method involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and target disassociate from each other, or melt. In another example, the method involves detecting a signal, such as a detectable label, present on one or both complementary strands.

The binding between an oligomer and its target nucleic acid is frequently characterized by the temperature ($T_m$) at which 50% of the oligomer is melted from its target. A higher ($T_m$) means a stronger or more stable complex relative to a complex with a lower ($T_m$).

Complement component 2 (C2): Part of the classical pathway of the complement system. Activated C1 cleaves C2 into C2a and C2b. C2a leads to activation of C3. Deficiency of C2 has been reported to be associated with certain autoimmune diseases, including systemic lupus erythematosus, Henoch-Schonlein purpura, or polymyositis. C2 is a member of EC 3.4.21.43. It is also known as classical-complement-pathway C3/C5 convertase.

Complement Factor H: Otherwise known as beta-1H; a serum glycoprotein that controls the function of the alternative complement pathway and acts as a cofactor with factor I (C3b inactivator). It regulates the activity of the C3 convertases such as C4b2a.

Complementarity and percentage complementarity: Molecules with complementary nucleic acids form a stable duplex or triplex when the strands bind, (hybridize), to each other by forming Watson-Crick, Hoogsteen or reverse Hoogsteen base pairs. Stable binding occurs when an oligonucleotide molecule remains detectably bound to a target nucleic acid sequence under the required conditions.

Complementarity is the degree to which bases in one nucleic acid strand base pair with the bases in a second nucleic acid strand. Complementarity is conveniently described by percentage, that is, the proportion of nucleotides that form base pairs between two strands or within a specific region or domain of two strands. For example, if 10 nucleotides of a 15-nucleotide oligonucleotide form base pairs with a targeted region of a DNA molecule, that oligonucleotide is said to have 66.67% complementarity to the region of DNA targeted.

In the present disclosure, "sufficient complementarity" means that a sufficient number of base pairs exist between an oligonucleotide molecule and a target nucleic acid sequence (such as a CFH, BF or C2 sequence) to achieve detectable binding. When expressed or measured by percentage of base pairs formed, the percentage complementarity that fulfills this goal can range from as little as about 50% complementarity to full (100%) complementary. In general, sufficient complementarity is at least about 50%, for example at least about 75% complementarity, at least about 90% complementarity, at least about 95% complementarity, at least about 98% complementarity, or even at least about 100% complementarity.

A thorough treatment of the qualitative and quantitative considerations involved in establishing binding conditions that allow one skilled in the art to design appropriate oligonucleotides for use under the desired conditions is provided by Beltz et al. (1983) *Methods Enzymol* 100:266-285; and by Sambrook et al. (ed.), *Molecular Cloning: A Laboratory Manual,* 2nd ed., vol. 1-3, Cold Spring Harbor Laboratory Press, Cold Spring Harbor, N.Y., 1989.

DNA (deoxyribonucleic acid): A long chain polymer which includes the genetic material of most living organisms (some viruses have genes including ribonucleic acid, RNA). The repeating units in DNA polymers are four different nucleotides, each of which includes one of the four bases (adenine, guanine, cytosine and thymine) bound to a deoxyribose sugar to which a phosphate group is attached. Triplets of nucleotides, referred to as codons, in DNA molecules code for amino acid in a polypeptide. The term codon is also used for the corresponding (and complementary) sequences of three nucleotides in the mRNA into which the DNA sequence is transcribed.

Drusen: Deposits that accumulate between the RPE basal lamina and the inner collagenous layer of Bruch's membrane (see, for example, van der Schaft et al. (1992) *Ophthalmol.* 99:278-86; Spraul et al. (1997) *Arch. Ophthalmol.* 115:267-73; and Mullins et al., Histochemical comparison of ocular "drusen" in monkey and human, In M. LaVail, J. Hollyfield, and R. Anderson (Eds.), in Degenerative Retinal Diseases (pp. 1-10). New York: Plenum Press, 1997). Hard drusen are small distinct deposits comprising homogeneous eosinophilic material and are usually round or hemispherical, without sloped borders. Soft drusen are larger, usually not homogeneous, and typically contain inclusions and spherical profiles. Some drusen may be calcified. The term "diffuse drusen," or "basal linear deposit," is used to describe amorphous material which forms a layer between the inner collagenous layer of Bruch's membrane and the retinal pigment epithelium (RPE). This material can appear similar to soft drusen histologically, with the exception that it is not mounded.

Factor B (BF): A proactivator of complement 3 in the alternate pathway of complement activation. Factor b is converted by factor d to c3 convertase. BF is a member of EC 3.4.21.47. Factor B circulates in the blood as a single chain polypeptide. Upon activation of the alternative pathway, it is cleaved by complement factor d yielding the noncatalytic chain Ba and the catalytic subunit Bb. The active subunit Bb is a serine protease which associates with C3b to form the alternative pathway C3 convertase. BF is also known as alternative-complement-pathway C3/C5 convertase.

Genetic predisposition or risk: Susceptibility of a subject to a genetic disease, such as AMD. However, such susceptibility may or may not result in actual development of the disease.

Haplotype: The genetic constitution of an individual chromosome. In diploid organisms, a haplotype contains one member of the pair of alleles for each site. A haplotype can refer to only one locus or to an entire genome. Haplotype can also refer to a set of single nucleotide polymorphisms (SNPs) found to be statistically associated on a single chromatid.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between to distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the Na+ and/or Mg++ concentration) of the hybridization buffer will determine the stringency of hybridization, though wash times also influence stringency. Calculations regarding hybridization conditions required for attaining particular degrees of stringency are discussed by Sambrook et al. (ed.), *Molecular Cloning: A Laboratory Manual,* 2nd ed., vol. 1-3, Cold Spring Harbor Laboratory Press, Cold Spring Harbor, N.Y., 1989, chapters 9 and 11; and Ausubel et al. Short Protocols in Molecular Biology, 4th ed., John Wiley & Sons, Inc., 1999.

For purposes of the present disclosure, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 20% mismatch will not hybridize. Conditions of "very high stringency" are those under which sequences with more than 10% mismatch will not hybridize.

The following is an exemplary set of hybridization conditions and is not meant to be limiting:

| Very High Stringency (detects sequences that share 90% identity) | |
|---|---|
| Hybridization: | 5x SSC at 65° C. for 16 hours |
| Wash twice: | 2x SSC at room temperature (RT) for 15 minutes each |
| Wash twice: | 0.5x SSC at 65° C. for 20 minutes each |
| High Stringency (detects sequences that share 80% identity or greater) | |
| Hybridization: | 5x-6x SSC at 65° C.-70° C. for 16-20 hours |
| Wash twice: | 2x SSC at RT for 5-20 minutes each |
| Wash twice: | 1x SSC at 55° C.-70° C. for 30 minutes each |
| Low Stringency (detects sequences that share greater than 50% identity) | |
| Hybridization: | 6x SSC at RT to 55° C. for 16-20 hours |
| Wash at least twice: | 2x-3x SSC at RT to 55° C. for 20-30 minutes each |

Isolated: An "isolated" biological component (such as a nucleic acid molecule, protein, or organelle) has been substantially separated or purified away from other biological components in the cell of the organism in which the component naturally occurs, such as other chromosomal and extrachromosomal DNA and RNA, proteins and organelles.

Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules and proteins.

Linkage disequilibrium (LD): The non-random association of alleles at two or more loci, not necessarily on the same chromosome. LD describes a situation in which some combinations of alleles or genetic markers occur more or less frequently in a population than would be expected from a random formation of haplotypes from alleles based on their frequencies. The expected frequency of occurrence of two alleles that are inherited independently is the frequency of the first allele multiplied by the frequency of the second allele. Alleles that co-occur at expected frequencies are said to be in linkage equilibrium.

Locus: The position of a gene (or other significant sequence) on a chromosome.

Mutation: Any change of the DNA sequence within a gene or chromosome. In some instances, a mutation will alter a characteristic or trait (phenotype), but this is not always the case. Types of mutations include base substitution point mutations (e.g., transitions or transversions), deletions, and insertions. Missense mutations are those that introduce a different amino acid into the sequence of the encoded protein; nonsense mutations are those that introduce a new stop codon. In the case of insertions or deletions, mutations can be in-frame (not changing the frame of the overall sequence) or frame shift mutations, which may result in the misreading of a large number of codons (and often leads to abnormal termination of the encoded product due to the presence of a stop codon in the alternative frame).

This term specifically encompasses variations that arise through somatic mutation, for instance those that are found only in disease cells, but not constitutionally, in a given individual. Examples of such somatically-acquired variations include the point mutations that frequently result in altered function of various genes that are involved in development of cancers. This term also encompasses DNA alterations that are present constitutionally, that alter the function of the encoded protein in a readily demonstrable manner, and that can be inherited by the children of an affected individual. In this respect, the term overlaps with "polymorphism," as defined below, but generally refers to the subset of constitutional alterations.

Nucleic acid molecule: A polymeric form of nucleotides, which may include both sense and anti-sense strands of RNA, CDNA, genomic DNA, and synthetic forms and mixed polymers of the above. A nucleotide refers to a ribonucleotide, deoxynucleotide or a modified form of either type of nucleotide. A "nucleic acid molecule" as used herein is synonymous with "nucleic acid" and "polynucleotide." A nucleic acid molecule is usually at least 10 bases in length, unless otherwise specified. The term includes single and double stranded forms of DNA. A polynucleotide may include either or both naturally occurring and modified nucleotides linked together by naturally occurring and/or non-naturally occurring nucleotide linkages.

Nucleotide: Includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: A nucleic acid molecule generally comprising a length of 300 bases or fewer. The term often refers to single stranded deoxyribonucleotides, but it can refer as well to single or double stranded ribonucleotides, RNA:DNA hybrids and double stranded DNAs, among others. The term "oligonucleotide" also includes oligonucleosides (that is, an oligonucleotide minus the phosphate) and any other organic base polymer. In some examples, oligonucleotides are about 10 to about 90 bases in length, for example, 12, 13, 14, 15, 16, 17, 18, 19 or 20 bases in length. Other oligonucleotides are about 25, about 30, about 35, about 40, about 45, about 50, about 55, about 60 bases, about 65 bases, about 70 bases, about 75 bases or about 80 bases in length. Oligonucleotides may be single stranded, for example, for use as probes or primers, or may be double stranded, for example, for use in the construction of a mutant gene. Oligonucleotides can be either sense or anti sense oligonucleotides. An oligonucleotide can be modified as discussed above in reference to nucleic acid molecules. Oligonucleotides can be obtained from existing nucleic acid sources (for example, genomic or cDNA), but can also be synthetic (for example, produced by laboratory or in vitro oligonucleotide synthesis).

Polymorphism: A variation in the gene sequence. The polymorphisms can be those variations (DNA sequence differences) which are generally found between individuals or different ethnic groups and geographic locations which, while having a different sequence, produce functionally equivalent gene products. The term can also refer to variants in the sequence which can lead to gene products that are not functionally equivalent. Polymorphisms also encompass variations which can be classified as alleles and/or mutations which can produce gene products which may have an altered function. Polymorphisms also encompass variations which can be classified as alleles and/or mutations which either produce no gene product or an inactive gene product or an active gene product produced at an abnormal rate or in an inappropriate tissue or in response to an inappropriate stimulus. Further, the term is also used interchangeably with allele as appropriate.

Polymorphisms can be referred to, for instance, by the nucleotide position at which the variation exists, by the change in amino acid sequence caused by the nucleotide variation, or by a change in some other characteristic of the nucleic acid molecule or protein that is linked to the variation.

Probes and Primers: A probe comprises an identifiable, isolated nucleic acid that recognizes a target nucleic acid sequence. Probes include a nucleic acid that is attached to an addressable location, a detectable label or other reporter molecule and that hybridizes to a target sequence. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example, in Sambrook et al. (ed.), Molecular Cloning: A Laboratory Manual, 2nd ed., vol. 1-3, Cold Spring Harbor Laboratory Press, Cold Spring Harbor, N.Y., 1989 and Ausubel et al. Short Protocols in Molecular Biology, 4th ed., John Wiley & Sons, Inc., 1999.

Primers are short nucleic acid molecules, for instance DNA oligonucleotides 10 nucleotides or more in length, for example that hybridize to contiguous complementary nucleotides or a sequence to be amplified. Longer DNA oligonucleotides may be about 15, 20, 25, 30 or 50 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, for example, by the PCR or other nucleic-acid amplification methods known in the art, as described below.

Methods for preparing and using nucleic acid probes and primers are described, for example, in Sambrook et al. (ed.), Molecular Cloning: A Laboratory Manual, 2nd ed., vol. 1-3, Cold Spring Harbor Laboratory Press, Cold Spring Harbor, N.Y., 1989; Ausubel et al. Short Protocols in Molecular Biology, 4th ed., John Wiley & Sons, Inc., 1999; and Innis et al. PCR Protocols, A Guide to Methods and Applications, Academic Press, Inc., San Diego, Calif., 1990. Amplification primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular probe or primer increases with its length. Thus, in order to obtain greater specificity, probes and primers can be selected that include at least 20, 25, 30, 35, 40, 45, 50 or more consecutive nucleotides of a target nucleotide sequences.

Sample: A sample obtained from a human or non-human mammal subject. As used herein, biological samples include all samples useful for genetic analysis in subjects, including, but not limited to: cells, tissues, and bodily fluids, such as blood; derivatives and fractions of blood (such as serum or plasma); extracted galls; biopsied or surgically removed tissue, including tissues that are, for example, unfixed, frozen, fixed in formalin and/or embedded in paraffin; tears; milk; skin scrapes; surface washings; urine; sputum; cerebrospinal fluid; prostate fluid; pus; bone marrow aspirates; BAL; saliva; cervical swabs; vaginal swabs; and oropharyngeal wash.

Single Nucleotide Polymorphism or SNP: A DNA sequence variation, occurring when a single nucleotide: adenine (A), thymine (T), cytosine (C) or guanine (G)—in the genome differs between members of the species. As used herein, the term "single nucleotide polymorphism" (or SNP) includes mutations and polymorphisms. SNPs may fall within coding sequences (CDS) of genes or between genes (intergenic regions). SNPs within a CDS change the codon, which may or may not change the amino acid in the protein sequence. The former may constitute different alleles. The latter are called silent mutations and typically occur in the third position of the codon (called the wobble position).

Subject: Human and non-human mammals (such as veterinary subjects).

Methods for Identifying a Subject at Increased Risk for AMD

Methods are provided for identifying a subject at increased risk of developing age-related macular degeneration (AMD). These methods include analyzing the subject's factor B (BF) and/or complement component 2 (C2) genes, and determining whether the subject has at least one protective polymorphism, wherein the protective polymorphism is selected from the group consisting of: a) R32Q in BF (rs641153); b) L9H in BF (rs4151667); c) IVS 10 in C2 (rs547154); and d) E318D in C2 (rs9332739). If the subject does not have at least one protective polymorphism, the subject is at increased risk for developing AMD. The method may further include analyzing the subject's CFH gene, or any other desired gene. As described herein, the delTT polymorphism in the CFH gene has been identified as being protective for AMD.

The methods may also include analyzing the subject's genotype at either the BF or C2 locus and at the CFH locus, and determining if the subject has at least one protective genotype selected from the group consisting of: a) heterozygous for the R32Q polymorphism in BF (rs641153); b) heterozygous for the L9H polymorphism in BF (rs4151667); c) heterozygous for the IVS 10 polymorphism in C2 (rs547154); d) heterozygous for the E318D polymorphism in C2 (rs9332739); e) homozygous for the delTT polymorphism in CFH; and f) homozygous for the R150R polymorphism in BF (rs1048709) and homozygous for Y402 in CFH; wherein if the subject does not have at least one protective genotype, the subject is at increased risk for developing AMD. The method may alternatively include analyzing the subject's genotype at both the BF and C2 locus, and at the CFH locus. The methods provided herein are also useful for identifying a subject at decreased risk of developing AMD, by determining if the subject has at least one of the above-identified polymorphisms or genotypes.

The analysis of a subject's genetic material for the presence or absence of particular polymorphisms is performed by obtaining a sample from the subject. This sample may be from any part of the subject's body that DNA or RNA can be isolated from Analysis may also be performed on protein isolated from a sample. Examples of such samples are discussed in more detail below. The subject may have been diagnosed with AMD, including early AMD, choroidal neovascularization, or geographic atrophy. The subject may have symptoms of AMD, such as drusen, pigmentary alterations, exudative changes such as hemorrhages, hard exudates, or subretinal/sub-RPE/intraretinal fluid, decreased visual acuity, blurred vision, distorted vision (metamorphopsia), central scotomas, or trouble discerning colors. Alternatively, the subject may not have been diagnosed with AMD, but may be in a high risk group, based on family history, age, race, or lifestyle choices. These lifestyle choices include, but are not limited to, smoking, exposure to sunlight (especially blue light), hypertension, cardiovascular risk factors such as high cholesterol and obesity, high fat intake, and oxidative stress. Subjects at risk for developing AMD also include those that are heterozygous or homozygous for the risk haplotype Y402H in the CFH gene.

Techniques for determining the presence or absence of a particular polymorphism or genotype of interest are well known in the art. Examples of these methods are discussed below, and the particular method used is not intended to be limiting. In addition, analyzing a subject's BF, C2 or CFH genes for the particular polymorphisms disclosed herein is also intended to include detection of any mutations that confer the same amino acid change as found in the polymorphism. For example, the L9H polymorphism in BF changes the nucleotide codon for the $9^{th}$ amino acid from CTC to CAC, generating a histidine instead of a leucine. This change could also be specified by the nucleotide codon CAT. The E318D polymorphism in C2 changes the nucleotide codon for the $318^{th}$ amino acid from GAG to GAC, generating an aspartic acid instead of a glutamic acid. This change could also be specified by the nucleotide codon GAT. The R150R polymorphism in BF changes the nucleotide codon for the $150^{th}$ amino acid from CGG to CGA. This change does not change the amino acid encoded (arginine). Arginine could also be encoded by CGT or CGC. In addition, arginine could be encoded by AGA or AGG. The Y402H polymorphism in CFH changes the nucleotide codon for the $402^{nd}$ amino acid from a TAT to a CAT, generating a histidine instead of a tyrosine. This change could also be specified by the nucleotide codon CAC. Any of these nucleotide codons, or others capable of being identified by one of skill in the art, can be detected in a subject.

The methods of the invention may identify at least about 5%, about 10%, about 15%, about 20%, about 25%, about 30%, about 35%, about 40%, about 45%, about 50%, about 55%, about 60%, about 65%, about 70% of subjects that will develop AMD.

AMD Preventative Therapy

The present disclosure also provides methods of avoiding or reducing the incidence of AMD in a subject determined to be genetically predisposed to developing AMD. For example, if in using the methods described above a mutation or protective polymorphism in the BF, C2 and/or CFH genes is not identified in a subject at risk for AMD based on any of the risk factors described above, a lifestyle choice may be undertaken by the subject in order to avoid or reduce the incidence of AMD or to delay the onset of AMD. For example, the subject may quit smoking; modify diet to include less fat intake; increase the intake of antioxidants, including vitamins C and E, beta-carotene, and zinc; or take prophylactic doses of agents that retard the development of retinal neovascularization. Treatment for such individuals could involve vaccines against certain pathogens, or antibiotics, or antiviral or fungal drugs. Treatment could also involve anti-inflammatory drugs, or complement inhibitors. In some examples, the treatment selected is specific and tailored for the subject, based on the analysis of that subject's genetic profile.

Methods for Detecting Known Polymorphisms

Methods for detecting known polymorphisms include, but are not limited to, restriction fragment length polymorphism (RFLP), single strand conformational polymorphism (SSCP) mapping, nucleic acid sequencing, hybridization, fluorescent in situ hybridization (FISH), PFGE analysis, RNase protection assay, allele-specific oligonucleotide (ASO), dot blot analysis, allele-specific PCR amplification (ARMS), oligonucleotide ligation assay (OLA) and PCR-SSCP. Also useful are the recently developed techniques of mass spectroscopy (such as Matrix Assisted Laser Desorption/Ionization (MALDI) or MALDI-Time Of Flight (MALDI-TOF); and DNA microchip technology for the detection of mutations. See, for example, Chapters 6 and 17 in *Human Molecular Genetics* 2. Eds. Tom Strachan and Andrew Read. New York: John Wiley & Sons Inc., 1999.

These techniques may include amplifying the nucleic acid before analysis. Amplification techniques are known to those of skill in the art and are discussed below.

When a polymorphism causes a nucleotide change that creates or abolishes the recognition site of a restriction enzyme, that restriction enzyme may be used to identify the polymorphism. Polymorphic alleles can be distinguished by PCR amplifying across the polymorphic site and digesting the PCR product with a relevant restriction endonuclease. The different products may be detected using a size fractionation method, such as gel electrophoresis. Alternatively, restriction fragment length polymorphism (RFLP) may be used. In cases where the polymorphism does not result in a restriction site difference, differences between alleles may be detected by amplification-created restriction site PCR. In this method, a primer is designed from sequence immediately adjacent to, but not encompassing, the restriction site. The primer is deliberately designed to have a single base mismatch in a noncritical position which does not prevent hybridization and amplification of both polymorphic sequences. This nucleotide mismatch, together with the sequence of the polymoiphic site creates a restriction site not present in one of the alleles.

Single strand conformational polymorphism (SSCP) mapping detects a band that migrates differentially because the sequence change causes a difference in single-strand, intramolecular base pairing. Single-stranded DNA molecules differing by only one base frequently show different electrophoretic mobilities in nondenaturing gels. Differences between normal and mutant DNA mobility are revealed by hybridization with labeled probes. This method does not detect all sequence changes, especially if the DNA fragment size is greater than about 500 bp, but can be optimized to detect most DNA sequence variation. The reduced detection sensitivity is a disadvantage, but the increased throughput possible with SSCP makes it an attractive alternative to direct sequencing for mutation detection on a research basis. The fragments which have shifted mobility on SSCP gels are then sequenced to determine the exact nature of the DNA sequence variation.

Direct DNA sequencing, either manual sequencing or automated fluorescent sequencing can detect sequence variation.

The detection of specific alleles may also be performed using Taq polymerase (Holland et al. (1991) *Proc. Natl. Acad. Sci. U.S.A.* 88:7276-80; Lee et al. (1999) *J. Mol. Biol.* 285: 73-83). This is based on the fact that Taq polymerase does not possess a proofreading 3' to 5' exonuclease activity, but possesses a 5' to 3' exonuclease activity. This assay involves the use of two conventional PCR primers (forward and reverse), which are specific for the target sequence, and a third primer, designed to bind specifically to a site on the target sequence downstream of the forward primer binding site. The third primer is generally labeled with two fluorophores, a reporter dye at the 5' end, and a quencher dye, having a different emission wavelength compared to the reporter dye, at the 3' end. The third primer also carries a blocking group at the 3' terminal nucleotide, so that it cannot by itself prime any new DNA synthesis. During the PCR reaction, Taq DNA polymerase synthesizes a new DNA strand primed by the forward primer and as the enzyme approaches the third primer, its 5' to 3' exonuclease activity processively degrades the third primer from its 5' end. The end result is that the nascent DNA strand extends beyond the third primer binding site and the reporter and quencher dyes are no longer bound to the same molecule. As the reporter dye is no longer near the quencher dye, the resulting increase in reporter emission intensity may be detected.

A polymorphism may be identified using one or more hybridization probes designed to hybridize with the particular polymorphism in the desired gene. A probe used for hybridization detection methods should be in some way labeled so as to enable detection of successful hybridization events. This may be achieved by in vitro methods such as nick-translation, replacing nucleotides in the probe by radioactively labeled nucleotides, or by random primer extension, in which non-labeled molecules act as a template for the synthesis of labeled copies. Other standard methods of labeling probes so as to detect hybridization are known to those skilled in the art.

For DNA fragments up to about 2 kb in length, single-base changes can be detected by chemical cleavage at the mismatched bases in mutant-normal heteroduplexes. For example, a strand of the DNA not including the polymorphism of interest is radiolabeled at one end and then is hybridized with a strand of the subject DNA. The resulting heteroduplex DNA is treated with hydroxylamine or osmium tetroxide, which modifies any C or C and T, respectively, in mismatched single-stranded regions; the modified backbone is susceptible to cleavage by piperidine. The shortened labeled fragment is detected by gel electrophoresis and autoradiography in comparison with DNA not including the polymorphism of interest.

Mismatches are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of samples. An example of a mismatch cleavage technique is the RNase protection method. This method involves the use of a labeled riboprobe which is complementary to one variation of the polymorphism being detected (generally the polymorphism not associated with protection from AMD). The riboprobe and either mRNA or DNA isolated from the subject are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the mRNA or gene but can be a segment of either. Alternatively, mismatches can be detected by shifts in the electrophoretic mobility of mismatched duplexes relative to matched duplexes.

DNA sequences of the BF, C2 or CFH genes which have been amplified by use of PCR may also be screened using allele-specific probes or oligonucleotides (ASO). These probes are nucleic acid oligomers, each of which contains a region of the gene sequence harboring a known mutation or polymorphism. For example, one oligomer may be about 30 nucleotides in length, corresponding to a portion of the BF, C2 or CFH gene sequence. By use of a battery of such allele-specific probes, PCR amplification products can be screened to identify the presence of one or more polymorphisms provided herein. Hybridization of allele-specific probes with amplified BF, C2 or CFH sequences can be performed, for example, on a nylon filter. Reverse dot-blotting may also be used. For example, a screen for more then one polymorphism may be performed using a series of ASOs specific for each polymorphic allele, spotted onto a single membrane which is then hybridized to labeled PCR-amplified test DNA. These assays may range from manually-spotted arrays of small numbers to very large ASO arrays on "gene chips" that can potentially detect large numbers of polymorphisms. Hybridization to a particular probe under high stringency hybridization conditions indicates the presence of the same polymorphism in the tissue as in the allele-specific probe. Such a technique can utilize probes which are labeled with gold nanopaiticles to yield a visual color result (Elghanian et al. (1997) *Science* 277:1078-81).

Allele-specific PCR amplification is based on a method called amplification refractory mutation system (ARMS) (Newton et al. (1989) *Nucleic Acids Res.* 17:2503-16). In this method, oligonucleotides with a mismatched 3'-residue will not function as primers in the PCR under appropriate conditions. Paired PCR reactions are carried out with two primers, one of which is a common primer, and one that exists in two slightly different versions, one specific for each polymorphism. The allele-specific primers are designed to be identical to the sequence of the two alleles over a region preceding the position of the variant nucleotide, up to and terminating in the variant nucleotide itself. Therefore, if the particular polymorphism or mutation is not present, an amplification product is not observed. In general, additional control primers are used to amplify an unrelated sequence. The location of the common primer can be designed to give products of different sizes for different polymorphisms, so that the PCR products from multiplexed reactions form a ladder on a gel. The polymorphism-specific primers may be label with different fluorescent or other labels, or may be given 5' extensions of different sizes. This method may be adapted for use in real-time PCR.

In the oligonucleotide ligation assay (OLA), two oligonucleotides are designed to hybridize to adjacent sequences in the target. The site at which they join is the site of the polymorphism. DNA ligase will join the two oligonucleotides only if they are perfectly hybridized (Nickerson et al. (1990) *Proc. Natl. Acad. Sci. U.S.A.* 87:8923-7). The assay may use various formats, including ELISA analysis or a fluorescence sequencher.

The technique of nucleic acid analysis using microchip technology may also be used. In this technique, potentially thousands of distinct oligonucleotide probes are built up in an array on a silicon chip. Nucleic acid to be analyzed is fluorescently labeled and hybridized to the probes on the chip. It is also possible to study nucleic acid-protein interactions using these nucleic acid microchips. Using this technique one can determine the presence of mutations or even sequence the nucleic acid being analyzed or one can measure expression levels of a gene of interest. The method is one of parallel processing of many, even thousands, of probes at once and can tremendously increase the rate of analysis.

Alteration of BF, C2 or CFH mRNA expression can be detected by any technique known in the art. These include Northern blot analysis, PCR amplification and RNase protection. Diminished mRNA expression indicates an alteration of the wild-type gene. Allele detection techniques may be protein based if a particular allele produces a protein with an amino acid variant. For example, epitopes specific for the amino acid variant can be detected with monoclonal antibodies. Alternatively, monoclonal antibodies immunoreactive with BF, C2 or CFH can be used to screen a tissue. Lack of cognate antigen would indicate a mutation. Antibodies specific for products of mutant alleles could also be used to detect mutant gene product. Such immunological assays can be done in any convenient formats known in the art. These include Western blots, immunohistochemical assays and ELISA assays. Any means for detecting an altered protein can be used to detect alteration of the wild-type BF, C2 or CFH gene. Functional assays, such as protein binding determinations, can be used. In addition, assays can be used which detect BF, C2 or CFH biochemical function. Finding a mutant BF, C2 or CFH gene product indicates alteration of a wild-type BF, C2 or CFH gene.

Amplification of Nucleic Acid Molecules

The nucleic acid samples obtained from the subject may be amplified from the clinical sample prior to detection. In one embodiment, DNA sequences are amplified. In another embodiment, RNA sequences are amplified.

Any nucleic acid amplification method can be used. In one specific, non-limiting example, polymerase chain reaction (PCR) is used to amplify the nucleic acid sequences associated with AMD. Other exemplary methods include, but are not limited to, RT-PCR and transcription-mediated amplification (TMA), cloning, polymerase chain reaction of specific alleles (PASA), ligase chain reaction, and nested polymerase chain reaction.

A pair of primers may be utilized in the amplification reaction. One or both of the primers can be labeled, for example with a detectable radiolabel, fluorophore, or biotin molecule. The pair of primers may include an upstream primer (which binds 5' to the downstream primer) and a downstream primer (which binds 3' to the upstream primer). The pair of primers used in the amplification reaction may be selective primers which permit amplification of a nucleic acid involved in AMD.

An additional pair of primers can be included in the amplification reaction as an internal control. For example, these primers can be used to amplify a "housekeeping" nucleic acid molecule, and serve to provide confirmation of appropriate amplification. In another example, a target nucleic acid molecule including primer hybridization sites can be constructed and included in the amplification reactor. One of skill in the art will readily be able to identify primer pairs to serve as internal control primers.

Amplification products may be assayed in a variety of ways, including size analysis, restriction digestion followed by size analysis, detecting specific tagged oligonucleotide primers in the reaction products, allele-specific oligonucleotide (ASO) hybridization, sequencing, hybridization, and the like.

PCR-based detection assays include multiplex amplification of a plurality of polymorphisms simultaneously. For example, it is well known in the art to select PCR primers to generate PCR products that do not overlap in size and can be analyzed simultaneously. Alternatively, it is possible to amplify different polymorphisms with primers that are differentially labeled and thus can each be detected. Other techniques are known in the art to allow multiplex analyses of a plurality of polymorphisms. A fragment of a gene may be amplified to produce copies and it may be determined whether copies of the fragment contain the particular protective polymorphism or genotype.

Immunodetection of Protective Proteins

In one embodiment of the invention, a protein assay is carried out to characterize polymorphisms in a subject's C2 or BF genes, e.g., to detect or identify protective proteins. Methods that can be adapted for detection of variant proteins are well known and include analytical biochemical methods such as electrophoresis (including capillary electrophoresis and two-dimensional electrophoresis), chromatographic methods such as high performance liquid chromatography (HPLC), thin layer chromatography (TLC), hyperdiffusion chromatography, mass spectrometry, and various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, western blotting and others.

For example, a number of well established immunological binding assay formats suitable for the practice of the invention are known (see, e.g., Harlow, E.; Lane, D. Antibodies: A laboratory manual. Cold Spring Harbor, N.Y.: Cold Spring Harbor Laboratory; 1988; and Ausubel et al., (2004) Current Protocols in Molecular Biology, John Wiley & Sons, New York N.Y. The assay may be, for example, competitive or non-competitive. Typically, immunological binding assays (or immunoassays) utilize a "capture agent" to specifically bind to and, often, immobilize the analyte. In one embodiment, the capture agent is a moiety that specifically binds to a variant C2 or BF polypeptide or subsequence. The bound protein may be detected using, for example, a detectably labeled anti-C2/BF antibody. In one embodiment, at least one of the antibodies is specific for the variant form (e.g., does not bind to the wild-type C2 or BF polypeptide.

Thus, in one aspect the method involves obtaining a biological sample from a subject (e.g., blood, serum, plasma, or urine); contacting the sample with a binding agent that distinguishes a protective and nonprotective form of C2 or BF, and detecting the formation of a complex between the binding agent and the nonprotective form of C2 or BF, if present. It will be understood that panels of antibodies may be used to detect protective proteins in a patient sample.

The invention also provides antibodies that specifically binds a protective C2 or DF protein but does not specifically bind a wild-type polypeptide (i.e., a C2 or BF protein not associated with protection). The antibodies bind an epitope found in only the protective form. For example, an antibody may not bind a wild-type BF (encoded by Genbank Accession Nos. NM_001710; AAB67977) or C2 (encoded by Genbank Accession Nos. NM_000063; NP_000054) but binds to a BF or C2 variant, as described above (i.e., a protein having one of the polymorphisms described herein as being protective for AMD). For example, the antibody may recognize a BF protein having glutamine at position 32 or histidine at position 9 or a C2 with an aspartic acid at position 318.

The antibodies can be polyclonal or monoclonal, and are made according to standard protocols. Antibodies can be made by injecting a suitable animal with a protective protein or fragments thereof. Monoclonal antibodies are screened according to standard protocols (Koehler and Milstein 1975, Nature 256:495; Dower et al., WO 91/17271 and McCafferty et al., WO 92/01047; and Vaughan et al., 1996, Nature Biotechnology, 14: 309; and references provided below). Monoclonal antibodies may be assayed for specific immunoreactivity with the protective polypeptide, but not the corresponding wild-type polypeptide, using methods known in the art. For methods, including antibody screening and subtraction methods; see Harlow & Lane, Antibodies, A Laboratory Manual, Cold Spring Harbor Press, New York (1988); Current Protocols in Immunology (J. E. Coligan et al., eds., 1999, including supplements through 2005); Goding, Monoclonal Antibodies, Principles and Practice (2d ed.) Academic Press, New York (1986); Burioni et al., 1998, "A new subtraction technique for molecular cloning of rare antiviral antibody specificities from phage display libraries" Res Virol. 149(5):327-30; Ames et al., 1994, Isolation of neutralizing anti-C5a monoclonal antibodies from a filamentous phage monovalent Fab display library. J. Immunol. 152(9): 4572-81; Shinohara et al., 2002, Isolation of monoclonal antibodies recognizing rare and dominant epitopes in plant vascular cell walls by phage display subtraction. J Immunol Methods 264(1-2):187-94. Immunization or screening can be directed against a full-length protective protein or, alternatively (and often more conveniently), against a peptide or polypeptide fragment comprising an epitope known to differ between the variant and wild-type forms. Antibodies can be expressed as tetramers containing two light and two heavy chains, as separate heavy chains, light chains, as Fab, Fab' F(ab')2, and Fv, or as single chain antibodies in which heavy and light chain variable domains are linked through a spacer.

Amplification of Nucleic Acid Molecules

The nucleic acid samples obtained from the subject may be amplified from the clinical sample prior to detection. In one embodiment, DNA sequences are amplified. In another embodiment, RNA sequences are amplified.

Any nucleic acid amplification method can be used. In one specific, non-limiting example, polymerase chain reaction (PCR) is used to amplify the nucleic acid sequences associated with AMD. Other exemplary methods include, but are not limited to, RT-PCR and transcription-mediated amplification (TMA), cloning, polymerase chain reaction of specific alleles (PASA), ligase chain reaction, and nested polymerase chain reaction.

A pair of primers may be utilized in the amplification reaction. One or both of the primers can be labeled, for example with a detectable radiolabel, fluorophore, or biotin molecule. The pair of primers may include an upstream primer (which binds 5' to the downstream primer) and a downstream primer (which binds 3' to the upstream primer). The pair of primers used in the amplification reaction may be selective primers which permit amplification of a nucleic acid involved in AMD.

An additional pair of primers can be included in the amplification reaction as an internal control. For example, these primers can be used to amplify a "housekeeping" nucleic acid molecule, and serve to provide confirmation of appropriate amplification. In another example, a target nucleic acid molecule including primer hybridization sites can be constructed and included in the amplification reactor. One of skill in the art will readily be able to identify primer pairs to serve as internal control primers.

Amplification products may be assayed in a variety of ways, including size analysis, restriction digestion followed by size analysis, detecting specific tagged oligonucleotide primers in the reaction products, allele-specific oligonucleotide (ASO) hybridization, sequencing, hybridization, and the like.

PCR-based detection assays include multiplex amplification of a plurality of polymorphisms simultaneously. For example, it is well known in the art to select PCR primers to generate PCR products that do not overlap in size and can be analyzed simultaneously. Alternatively, it is possible to amplify different polymorphisms with primers that are differentially labeled and thus can each be detected. Other techniques are known in the art to allow multiplex analyses of a plurality of polymorphisms. A fragment of a gene may be amplified to produce copies and it may be determined whether copies of the fragment contain the particular protective polymorphism or genotype.

Complement Factor H (CFH)

The CFH gene is located on chromosome 1 q in a region repeatedly linked to AMD in family-based studies. Recently, three independent studies have revealed that a polymorphism, a T→C substitution at nucleotide 1277 in exon 9, which results a tyrosine to histidine change (Y402H) in the complement factor H gene makes a substantial contribution to AMD susceptibility (Klein et al. (2005) *Science* 308:385-389; Haines et al. (2005) *Science.* 308:419-421; Edwards et al. (2005) *Science.* 308:421-424). These studies reported odd ratios for AMD ranging between 3.3 and 4.6 for carriers of the C allele and between 3.3 and 7.4 for CC homozygotes. Subsequently, this association was confirmed by two other studies (Zareparsi et al. (2005) *Am. J. Hum. Genet.* 77:149-153; Hageman et al. (2005) *Proc. Natl. Acad. Sci. U.S.A.* 102: 7227-7232). In one study, seven other common SNPs were found to be associated with AMD in addition to the Y402H polymorphism (Hageman et al. (2005) *Proc. Natl. Acad. Sci. U.S.A.* 102:7227-7232).

Pairwise linkage analysis showed that these seven polymorphisms were in linkage disequilibrium and one common at-risk haplotype with a set of these polymorphisms were detected in 50% of cases versus 29% of controls [OR=2.46, 95% CI (1.95-3.11)]. Homozygotes for this haplotype were found in 24.2% of cases and 8.3% of the controls. Also two common protective haplotypes were found in 34% of controls and 18% of cases [OR=0.48, 95% CI (0.33-0.69)] and [OR=0.54, 95% CI (0.33-0.69)].

Factor B and Complement Component 2

Activation of the alternative pathway is initiated by factor D-catalyzed cleavage of C3b-bound factor B (BF), resulting in the formation of the C3Bb complex (C3 convertase). This complex is stabilized by the regulatory protein properdin, whereas its dissociation is accelerated by regulatory proteins including CFH. BF and C2 are paralogous genes located only 500 bp apart on human chromosome 6p21. C2 functions in the classical complement pathway. These two genes, along with genes encoding complement components 4A (C4A) and 4B (C4B), comprise a "complotype" (complement haplotype) that occupies approximately 100-120 kb between HLA-B and HLA-DR/DQ in the major histocompatibility complex (MHC) class III region.

Clinical Samples

Appropriate samples for use with the current disclosure in determining a subject's genetic predisposition to AMD include any conventional clinical samples, including, but not limited to, blood or blood-fractions (such as serum or plasma), mouthwashes or buccal scrapes, chorionic villus biopsy samples, semen, Guthrie cards, eye fluid, sputum, lymph fluid, urine and tissue. Most simply, blood can be drawn and DNA (or RNA) extracted from the cells of the blood. Alteration of a wild-type BF, C2, and/or CFH allele, whether, for example, by point mutation or deletion, can be detected by any of the means discussed herein.

Techniques for acquisition of such samples are well known in the art (for example see Schluger et al. (1992) *J. Exp. Med.* 176:1327-33, for the collection of serum samples). Serum or other blood fractions can be prepared in the conventional manner. For example, about 200 µL of serum can be used for the extraction of DNA for use in amplification reactions.

Once a sample has been obtained, the sample can be used directly, concentrated (for example by centrifugation or filtration), purified, or combinations thereof, and an amplification reaction performed. For example, rapid DNA preparation can be performed using a commercially available kit (such as the InstaGene Matrix, BioRad, Hercules, Calif.; the NucliSens isolation kit, Organon Teknika, Netherlands). In one example, the DNA preparation method yields a nucleotide preparation that is accessible to, and amenable to, nucleic acid amplification.

Microarrays

In particular examples, methods for detecting a polymorphism in the BF, C2, and/or CFH genes use the arrays disclosed herein. Such arrays can include nucleic acid molecules. In one example, the array includes nucleic acid oligonucleotide probes that can hybridize to polymorphic BF, C2, and/or CFH gene sequences, such as those polymorphisms discussed herein. Certain of such arrays (as well as the methods described herein) can include other polymorphisms associated with risk or protection from developing AMD, as well as other sequences, such as one or more probes that recognize one or more housekeeping genes.

The arrays herein termed "AMD detection arrays," are used to determine the genetic susceptibility of a subject to developing AMD. In one example, a set of oligonucleotide probes is attached to the surface of a solid support for use in detection of a polymorphism in the BF, C2, and/or CFH genes, such as those amplified nucleic acid sequences obtained from the subject. Additionally, if an internal control nucleic acid sequence was amplified in the amplification reaction (see above), an oligonucleotide probe can be included to detect the presence of this amplified nucleic acid molecule.

The oligonucleotide probes bound to the array can specifically bind sequences amplified in an amplification reaction (such as under high stringency conditions). Oligonucleotides comprising at least 15, 20, 25, 30, 35, 40, or more consecutive nucleotides of the BF, C2, and/or CFH genes may be used.

The methods and apparatus in accordance with the present disclosure take advantage of the fact that under appropriate conditions oligonucleotides form base-paired duplexes with nucleic acid molecules that have a complementary base sequence. The stability of the duplex is dependent on a number of factors, including the length of the oligonucleotides, the base composition, and the composition of the solution in which hybridization is effected. The effects of base composition on duplex stability may be reduced by carrying out the hybridization in particular solutions, for example in the presence of high concentrations of tertiary or quaternary amines.

The thermal stability of the duplex is also dependent on the degree of sequence similarity between the sequences. By carrying out the hybridization at temperatures close to the anticipated $T_m$'s of the type of duplexes expected to be formed between the target sequences and the oligonucleotides bound to the array, the rate of formation of mismatched duplexes may be substantially reduced.

The length of each oligonucleotide sequence employed in the array can be selected to optimize binding of target BF, C2, and/or CFH nucleic acid sequences. An optimum length for use with a particular BF, C2, and/or CFH nucleic acid sequence under specific screening conditions can be determined empirically. Thus, the length for each individual element of the set of oligonucleotide sequences including in the array can be optimized for screening. In one example, oligonucleotide probes are from about 20 to about 35 nucleotides in length or about 25 to about 40 nucleotides in length.

The oligonucleotide probe sequences forming the array can be directly linked to the support, for example via the 5'- or 3'-end of the probe. In one example, the oligonucleotides are bound to the solid support by the 5' end. However, one of skill in the art can determine whether the use of the 3' end or the 5' end of the oligonucleotide is suitable for bonding to the solid support. In general, the internal complementarity of an oligonucleotide probe in the region of the 3' end and the 5' end determines binding to the support. Alternatively, the oligonucleotide probes can be attached to the support by non-BF, C2, and/or CFH sequences such as oligonucleotides or other molecules that serve as spacers or linkers to the solid support.

In another example, an array includes protein sequences, which include at least one BF, C2, and/or CFH protein (or genes, cDNAs or other polynucleotide molecules including one of the listed sequences, or a fragment thereof), or a fragment of such protein, or an antibody specific to such a protein or protein fragment. The proteins or antibodies forming the array can be directly linked to the support. Alternatively, the proteins or antibodies can be attached to the support by spacers or linkers to the solid support.

Abnormalities in BF, C2, and/or CFH proteins can be detected using, for instance, a BF, C2, and/or CFH protein-specific binding agent, which in some instances will be detectably labeled. In certain examples, therefore, detecting an abnormality includes contacting a sample from the subject with a BF, C2, and/or CFH protein-specific binding agent; and detecting whether the binding agent is bound by the sample and thereby measuring the levels of the BF, C2, and/or CFH protein present in the sample, in which a difference in the level of BF, C2, and/or CFH protein in the sample, relative to the level of BF, C2, and/or CFH protein found an analogous sample from a subject not predisposed to developing AMD, or a standard BF, C2, and/or CFH protein level in analogous samples from a subject not having a predisposition for developing AMD, is an abnormality in that BF, C2, and/or CFH molecule.

In particular examples, the microarray material is formed from glass (silicon dioxide). Suitable silicon dioxide types for the solid support include, but are not limited to: aluminosilicate, borosilicate, silica, soda lime, zinc titania and fused silica (for example see Schena, *Microarray Analysis*. John Wiley & Sons, Inc, Hoboken, N.J., 2003). The attachment of nucleic acids to the surface of the glass can be achieved by methods known in the art, for example by surface treatments that form from an organic polymer. Particular examples include, but are not limited to: polypropylene, polyethylene, polybutylene, polyisobutylene, polybutadiene, polyisoprene, polyvinylpyrrolidine, polytetrafluroethylene, polyvinylidene difluroide, polyfluoroethylene-propylene, polyethylenevinyl alcohol, polymethylpentene, polychlorotrifluoroethylene, polysulfones, hydroxylated biaxially oriented polypropylene, aminated biaxially oriented polypropylene, thiolated biaxially oriented polypropylene, etyleneacrylic acid, thylene methacrylic acid, and blends of copolymers thereof (see U.S. Pat. No. 5,985,567, herein incorporated by reference), organosilane compounds that provide chemically active amine or aldehyde groups, epoxy or polylysine treatment of the microarray. Another example of a solid support surface is polypropylene.

In general, suitable characteristics of the material that can be used to form the solid support surface include: being amenable to surface activation such that upon activation, the surface of the support is capable of covalently attaching a biomolecule such as an oligonucleotide thereto; amenability to "in situ" synthesis of biomolecules; being chemically inert such that at the areas on the support not occupied by the oligonucleotides are not amenable to non-specific binding, or when non-specific binding occurs, such materials can be readily removed from the surface without removing the oligonucleotides.

In one example, the surface treatment is amine-containing silane derivatives. Attachment of nucleic acids to an amine surface occurs via interactions between negatively charged phosphate groups on the DNA backbone and positively charged amino groups (Schena, Microarray Analysis. John Wiley & Sons, Inc, Hoboken, N.J., 2003, herein incorporated by reference). In another example, reactive aldehyde groups are used as surface treatment. Attachment to the aldehyde surface is achieved by the addition of 5'-amine group or amino linker to the DNA of interest. Binding occurs when the nonbonding electron pair on the amine linker acts as a nucleophile that attacks the electropositive carbon atom of the aldehyde group.

A wide variety of array formats can be employed in accordance with the present disclosure. One example includes a linear array of oligonucleotide bands, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use (see U.S. Pat. No. 5,981,185, herein incorporated by reference). In one example, the array is formed on a polymer medium, which is a thread, membrane or film. An example of an organic polymer medium is a polypropylene sheet having a thickness on the order of about 1 mm (0.001 inch) to about 20 mm, although the thickness of the film is not critical and can be varied over a fairly broad range. Particularly disclosed for preparation of arrays at this time are biaxially oriented polypropylene (BOPP) films; in addition to their durability, BOPP films exhibit a low background fluorescence. In a particular example, the array is a solid phase, Allele-Specific Oligonucleotides (ASO) based nucleic acid array.

The array formats of the present disclosure can be included in a variety of different types of formats. A "format" includes any format to which the solid support can be affixed, such as microtiter plates, test tubes, inorganic sheets, dipsticks, and the like. For example, when the solid support is a polypropylene thread, one or more polypropylene threads can be affixed to a plastic dipstick-type device; polypropylene membranes can be affixed to glass slides. The particular format is, in and of itself, unimportant. All that is necessary is that the solid support can be affixed thereto without affecting the functional behavior of the solid support or any biopolymer absorbed thereon, and that the format (such as the dipstick or slide) is stable to any materials into which the device is introduced (such as clinical samples and hybridization solutions).

The arrays of the present disclosure can be prepared by a variety of approaches. In one example, oligonucleotide or protein sequences are synthesized separately and then attached to a solid support (see U.S. Pat. No. 6,013,789, herein incorporated by reference). In another example, sequences are synthesized directly onto the support to provide the desired array (see U.S. Pat. No. 5,554,501, herein incorporated by reference). Suitable methods for covalently coupling oligonucleotides and proteins to a solid support and for directly synthesizing the oligonucleotides or proteins onto the support are known to those working in the field; a summary of suitable methods can be found in Matson et al. (1994) Anal. Biochem. 217:306-10. In one example, the oligonucleotides are synthesized onto the support using conventional chemical techniques for preparing oligonucleotides on solid supports (such as see PCT Publication Nos. WO 85/01051 and WO 89/10977, or U.S. Pat. No. 5,554,501, each of which are herein incorporated by reference).

A suitable array can be produced using automated means to synthesize oligonucleotides in the cells of the array by laying down the precursors for the four bases in a predetermined pattern. Briefly, a multiple-channel automated chemical delivery system is employed to create oligonucleotide probe populations in parallel rows (corresponding in number to the number of channels in the delivery system) across the substrate. Following completion of oligonucleotide synthesis in a first direction, the substrate can then be rotated by 90° to permit synthesis to proceed within a second (2°) set of rows that are now perpendicular to the first set. This process creates a multiple-channel array whose intersection generates a plurality of discrete cells.

In particular examples, the oligonucleotide probes on the array include one or more labels, that permit detection of oligonucleotide probe:target sequence hybridization complexes.

Kits

The present disclosure provides for kits that can be used to determine whether a subject, such as an otherwise healthy human subject, is genetically predisposed to AMD. Such kits allow one to determine if a subject has one or more genetic mutations or polymorphisms in BF, C2 or CFH gene sequences.

The kits contain reagents useful for determining the presence or absence of at least one polymorphism in a subject's BF, C2 or CFH genes, such as probes or primers that selectively hybridize to a BF, C2 or CFH polymorphic sequence identified herein. Such kits can be used with the methods described herein to determine a subject's BF, C2, or CFH genotype or haplotype.

Oligonucleotide probes and/or primers may be supplied in the form of a kit for use in detection of a specific BF, C2, or CFH sequence, such as a SNP or haplotype described herein, in a subject. In such a kit, an appropriate amount of one or more of the oligonucleotide primers is provided in one or more containers. The oligonucleotide primers may be provided suspended in an aqueous solution or as a freeze-dried or lyophilized powder, for instance. The container(s) in which the oligonucleotide(s) are supplied can be any conventional container that is capable of holding the supplied form, for instance, microfuge tubes, ampoules, or bottles. In some applications, pairs of primers may be provided in pre-measured single use amounts in individual, typically disposable, tubes or equivalent containers. With such an arrangement, the sample to be tested for the presence of a BF, C2, or CFH polymorphism can be added to the individual tubes and amplification carried out directly.

The amount of each oligonucleotide primer supplied in the kit can be any appropriate amount, depending for instance on the market to which the product is directed. For instance, if the kit is adapted for research or clinical use, the amount of each oligonucleotide primer provided would likely be an amount sufficient to prime several PCR amplification reactions. Those of ordinary skill in the art know the amount of oligonucleotide primer that is appropriate for use in a single amplification reaction. General guidelines may for instance be found in Innis et al. (PCR Protocols, A Guide to Methods and Applications, Academic Press, Inc., San Diego, Calif., 1990), Sambrook et al. (In Molecular Cloning: A Laboratory Manual, Cold Spring Harbor, N.Y., 1989), and Ausubel et al. (In Current Protocols in Molecular Biology, Greene Publ. Assoc. and Wiley-Intersciences, 1992).

A kit may include more than two primers, in order to facilitate the in vitro amplification of BF, C2, or CFH-encoding sequences, for instance a specific target BF, C2, or CFH gene or the 5' or 3' flanking region thereof.

In some embodiments, kits may also include the reagents necessary to carry out nucleotide amplification reactions, including, for instance, DNA sample preparation reagents, appropriate buffers (e.g., polymerase buffer), salts (e.g., magnesium chloride), and deoxyribonucleotides (dNTPs).

Kits may in addition include either labeled or unlabeled oligonucleotide probes for use in detection of BF, C2, or CFH polymorphisms or haplotypes. In certain embodiments, these probes will be specific for a potential polymorphic site that may be present in the target amplified sequences. The appropriate sequences for such a probe will be any sequence that includes one or more of the identified polymorphic sites, such that the sequence the probe is complementary to a polymorphic site and the surrounding BF, C2, or CFH sequence. By way of example, such probes are of at least 6 nucleotides in length, and the polymorphic site occurs at any position within the length of the probe. It is often beneficial to use longer probes, in order to ensure specificity. Thus, in some embodiments, the probe is at least 8, at least 10, at least 12, at least 15, at least 20, at least 30 nucleotides or longer.

It may also be advantageous to provide in the kit one or more control sequences for use in the amplification reactions. The design of appropriate positive control sequences is well known to one of ordinary skill in the appropriate art. By way of example, control sequences may comprise human (or non-human) BF, C2, or CFH nucleic acid molecule(s) with known sequence at one or more target SNP positions, such as those described herein. Controls may also comprise non-BF, C2, or CFH nucleic acid molecules.

In some embodiments, kits may also include some or all of the reagents necessary to carry out RT-PCR in vitro amplification reactions, including, for instance, RNA sample preparation reagents (including for example, an RNase inhibitor), appropriate buffers (for example, polymerase buffer), salts (for example, magnesium chloride), and deoxyribonucleotides (dNTPs).

Such kits may in addition include either labeled or unlabeled oligonucleotide probes for use in detection of the in vitro amplified target sequences. The appropriate sequences for such a probe will be any sequence that falls between the annealing sites of the two provided oligonucleotide primers, such that the sequence the probe is complementary to is amplified during the PCR reaction. In certain embodiments, these probes will be specific for a potential polymorphism that may be present in the target amplified sequences.

It may also be advantageous to provide in the kit one or more control sequences for use in the RT-PCR reactions. The design of appropriate positive control sequences is well known to one of ordinary skill in the appropriate art.

Kits for the detection or analysis of BF, C2, or CFH protein expression (such as over- or under-expression, or expression of a specific isoform) are also encompassed. Such kits may include at least one target protein specific binding agent (for example, a polyclonal or monoclonal antibody or antibody fragment that specifically recognizes a BF, C2, or CFH protein, or a specific polymorphic form of a BF, C2, or CFH protein) and may include at least one control (such as a determined amount of target BF, C2, or CFH protein, or a sample containing a determined amount of BF, C2, or CFH protein). The BF, C2, or CFH-protein specific binding agent and control may be contained in separate containers. The antibodies may have the ability to distinguish between polymorphic forms of BF, CD and/or CFH protein.

BF, C2, or CFH protein or isoform expression detection kits may also include a means for detecting BF, C2, or CFH: binding agent complexes, for instance the agent may be detectably labeled. If the detectable agent is not labeled, it may be detected by second antibodies or protein A, for example, which may also be provided in some kits in one or more separate containers. Such techniques are well known.

Additional components in specific kits may include instructions for carrying out the assay. Instructions will allow the tester to determine BF, C2, or CFH expression level. Reaction vessels and auxiliary reagents such as chromogens, buffers, enzymes, etc. may also be included in the kits. The instructions can provide calibration curves or charts to compare with the determined (for example, experimentally measured) values.

Also provided are kits that allow differentiation between individuals who are homozygous versus heterozygous for specific SNPs (or haplotypes) of the BF, C2, or CFH genes as described herein. Examples of such kits provide the materials necessary to perform oligonucleotide ligation assays (OLA), as described in Nickerson et al. (1990) *Proc. Natl. Acad. Sci. U.S.A.* 87:8923-8927. In specific embodiments, these kits contain one or more microtiter plate assays, designed to detect polymorphism(s) in a BF, C2, or CFH sequence of a subject, as described herein. Instructions in these kits will allow the tester to determine whether a specified BF, C2, or CFH allele is present, and whether it is homozygous or heterozygous. It may also be advantageous to provide in the kit one or more control sequences for use in the OLA reactions. The design of appropriate positive control sequences is well known to one of ordinary skill in the appropriate art.

The kit may involve the use of a number of assay formats including those involving nucleic acid binding, such binding to filters, beads, or microtiter plates and the like. Techniques may include dot blots, RNA blots, DNA blots, PCR, RFLP, and the like.

Microarray-based kits are also provided. These microarray kits may be of use in genotyping analyses. In general, these kits include one or more oligonucleotides provided immobilized on a substrate, for example at an addressable location. The kit also includes instructions, usually written instructions, to assist the user in probing the array. Such instructions can optionally be provided on a computer readable medium Kits may additionally include one or more buffers for use during assay of the provided array. For instance, such buffers may include a low stringency wash, a high stringency wash, and/or a stripping solution. These buffers may be provided in bulk, where each container of buffer is large enough to hold sufficient buffer for several probing or washing or stripping procedures. Alternatively, the buffers can be provided in pre-measured aliquots, which would be tailored to the size and style of array included in the kit. Certain kits may also provide one or more containers in which to carry out array-probing reactions.

Kits may in addition include one or more containers of detector molecules, such as antibodies or probes (or mixtures of antibodies, mixtures of probes, or mixtures of the antibodies and probes), for detecting biomolecules captured on the array. The kit may also include either labeled or unlabeled control probe molecules, to provide for internal tests of either the labeling procedure or probing of the array, or both. The control probe molecules may be provided suspended in an aqueous solution or as a freeze-dried or lyophilized powder, for instance. The container(s) in which the controls are supplied can be any conventional container that is capable of holding the supplied form, for instance, microfuge tubes, ampoules, or bottles. In some applications, control probes may be provided in pre-measured single use amounts in individual, typically disposable, tubes or equivalent containers.

The amount of each control probe supplied in the kit can be any particular amount, depending for instance on the market to which the product is directed. For instance, if the kit is adapted for research or clinical use, sufficient control probe(s) likely will be provided to perform several controlled analyses of the array. Likewise, where multiple control probes are provided in one kit, the specific probes provided will be tailored to the market and the accompanying kit. In certain embodiments, a plurality of different control probes will be provided in a single kit, each control probe being from a different type of specimen found on an associated array (for example, in a kit that provides both eukaryotic and prokaryotic specimens, a prokaryote-specific control probe and a separate eukaryote-specific control probe may be provided).

In some embodiments of the current invention, kits may also include the reagents necessary to carry out one or more probe-labeling reactions. The specific reagents included will be chosen in order to satisfy the end user's needs, depending on the type of probe molecule (for example, DNA or RNA) and the method of labeling (for example, radiolabel incorporated during probe synthesis, attachable fluorescent tag, etc.).

Further kits are provided for the labeling of probe molecules for use in assaying arrays provided herein. Such kits may optionally include an array to be assayed by the so labeled probe molecules.

The disclosure is illustrated by the following non-limiting Examples.

EXAMPLES

Example 1

Materials and Methods

Subjects: Two independent groups of AMD cases and age-matched controls of European-American descent over the age of 60 were used in this study. These groups consisted of 350 unrelated subjects with clinically documented AMD (mean age 79.5+/−7.8) and 114 unrelated, control individuals (mean age 78.4+/−7.4; matched by age and ethnicity) from the University of Iowa, and 548 unrelated subjects with clinically documented AMD (mean age 71.32+/−8.9 years), and 275 unrelated, matched by age and ethnicity, controls (mean age 68.84+/−8.6 years) from Columbia University. Subjects were examined by trained ophthalmologists.

Stereoscopic fundus photographs were graded according to standardized classification systems as described in Hageman, 2005, supra; Bird et al. (1995) *Surv. Ophthalmol.* 39:367-74; and Klaver et al. (2001) *Invest. Ophthalmol. Vis. Sci.* 42:2237-41. Controls did not exhibit any distinguishing signs of macular disease nor did they have a known family history of AMD (stages 0 and 1a). AMD subject were subdivided into phenotypic categories based on the classification of their most severe eye at the time of their recruitment. Genomic DNA was generated from peripheral blood leukocytes using QIAamp DNA Blood Maxi kits (Qiagen, Valencia, Calif.).

Studies were conducted under the protocols approved by the Institutional Review Boards of Columbia University and the University of Iowa. Informed consent was obtained from all study subjects prior to participation.

Immunohistochemistry: Posterior poles were processed, sectioned and labeled with antibody directed against factor Ba (Quidel), as described in Anderson et al. (2002) *Am. J. Ophthalmol.* 134:411-31. Adjacent sections were incubated with secondary antibody alone, to serve as controls. Some immunolabeled specimens were prepared and viewed by confocal laser scanning microscopy, as described (Anderson et al., 2002, supra).

Mutation Screening and Analysis: Coding and adjacent intronic regions of BF and C2 were examined for variants using SSCP analyses, denaturing high performance liquid chromatography (DHPLC) and direct sequencing. Primers for SSCP, DHPLC and DNA sequencing analyses were designed to amplify each exon and its adjacent intronic regions using MACVECTOR™ software (San Diego, Calif.). PCR-derived amplicons were screened for sequence variation, as described in Allikmets et al. (1997) *Science* 277: 1805-1807 and in Hayashi et al. (2004) *Ophthalmic Genet.* 25:111-9. All changes detected by SSCP and DHPLC were confirmed by bidirectional sequencing according to standard protocols.

Genotyping: Single nucleotide polymorphisms (SNPs) were discovered through data mining (Ensembl database, dbSNP; Celera Discovery System) and through sequencing. Assays for variants with greater than 10% frequency in test populations were purchased from Applied Biosystems as Validated, Inventoried SNP Assays-On-Demand, or submitted to an Applied Biosystems Assays-By-Design pipeline. The technique employed was identical to that described in Hageman et al., 2005, supra. Briefly, 5 ng of DNA were subjected to 50 cycles on an ABI 9700 384-well thermocycler, and plates were read in an Applied Biosystems 7900 HT Sequence Detection System.

Statistical Analysis: Genotypes were tabulated in Microsoft EXCEL and presented to SPSS (SPSS, Inc.) for contingency table analysis as described in Hageman et al., 2005, supra, and Klaver et al., 2001, supra. Compliance to Hardy7 Weinberg Equilibrium was checked using SAS/Genetics (SAS Institute, Inc., Cary, N.C.), and all SNPs in both cases and controls survived a cut off of p<0.05. For haplotype estimation we used snphap (written by David Clayton; Cambridge Institute for Medical Research, Cambridge, United Kingdom), downloaded from the Cambridge Institute for Medical Research website http://www-gene.cimr.cam.ac.uk/clayton/software/), SNPEM (Written by Dr. Nicholas Schork and M. Daniele Fallin and obtained from D. Fallin), and PHASE version 2.11 (written by Matthew Stephens; University of Washington, Seattle, Wash., and available from his web site at www.stat.washington.edu/stephens/software-.html). The haplotype analysis strategy used was first to obtain haplotype estimates using the Expectation Maximization (EM) or Gibbs sampling algorithm, second, to identify htSNPs representing a minimal informative set within a region of linkage disequilibrium, and third, to assess these for significant association with AMD. Linkage disequilibrium was assessed (not shown) using the graphical tools available at the Innate Immunity PGA website (www.innateimmunity-.net). All p-values are two-tailed and X2 values are presented as asymptotic significance. Overall type I error rates ($\alpha$), were retrospectively calculated using the method of Benjamini and Hochberg (1995) *J. R. Stat. Soc. Ser. B* 57:289-300 as implemented at the Innate Immunity PGA website (https://innate-immunity.net/IIPGA2/Bioinformatics/multipletestfdrform), and were below $2 \times 10^{-3}$.

Figure 2B:
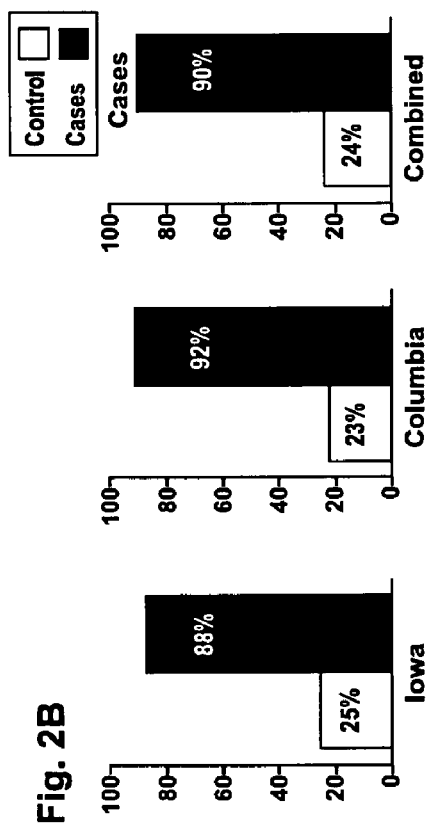
FIG. 2 shows combined complement gene analyses. Individual SNP analyses revealed several possible combinations of SNPs that protect an individual from developing AMD. To test these, an empirical model was first applied.
FIG. 2A shows a model graphic, interpreted as giving four possible combinations of genotypes that would protect from AMD. These are: (1) rs641153 (R32Q) is G/A and rs1061170 (Y402H) is C/T; (2) rs547154 is G/A and rs1061170 is C/C; (3) rs4151667 (L9H) is T/A and rs1061170 is C/T; (4) rs4151667 is T/A and rs1061170 is C/C. Application of this model resulted in the distributions shown in FIG. 2B for the Iowa, Columbia, and combined cohorts, respectively. These distributions were subjected to Fisher's exact test and evidenced p-values of P=0.00237, P=4.28×10$^{-8}$ and P=7.90×10$^{-10}$. For comparative purposes, Exemplar software generated a protective model that provided a "best fit" to the data using a machine-learning method know as Genetic Algorithms. The resulting best performing model is depicted in FIG. 2C. This model describes four possible individual or combinations of genotypes that protect from AMD; i.e., combinations resulting in the model being "true." These genotypes are: (1) rs1048709 (R150R) is G/G and rs1061170 is C/C; or (2) rs547154 is G/A; or (3) rs4151667 is T/A; or (4) CFH intron 1 variant is delTT. The model performance is shown in FIG. 2D for the Iowa, Columbia, and combined cohorts. These distributions evidenced p-values of P=7.49×10$^{-5}$, P=2.97×10$^{-22}$ and P=1.69×10$^{-23}$, respectively.
Figure 2A:
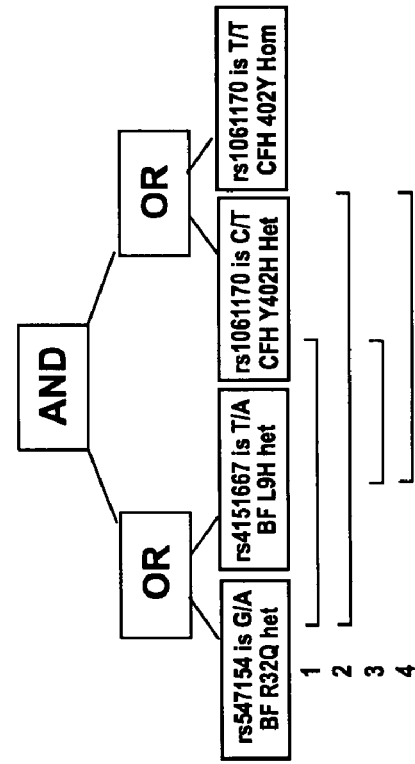
Figure 2D:
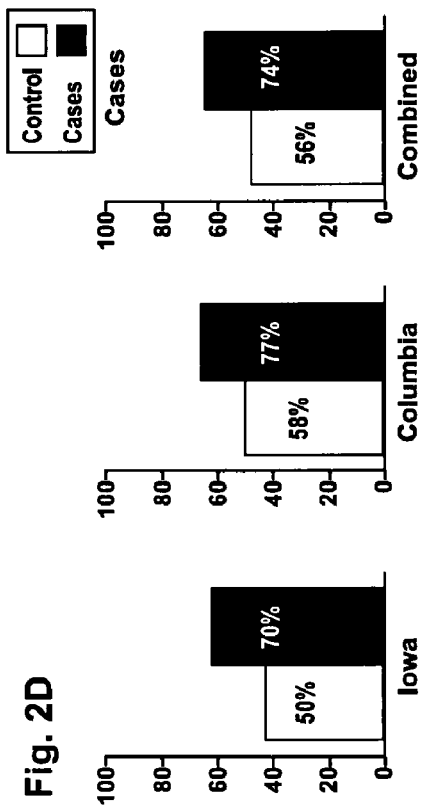
Figure 2C:
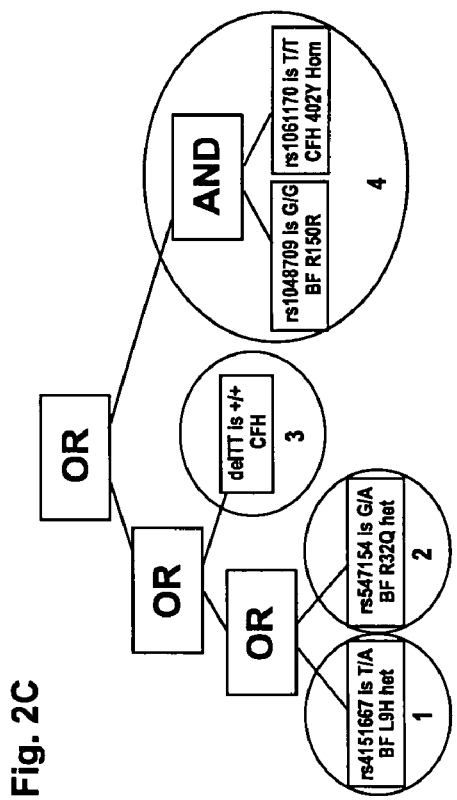

Significant haplotypes were subjected to permutation testing in both SNPEM and PHASE. The protective SNP model drawn in FIG. 2A was presented to Exemplar 2.2 (available on the Sapio sciences website at http://www.sapiosciences.com) and statistically evaluated by that software for fitness against the three datasets (Iowa, Columbia and Combined) presented in FIG. 2B. Generation of the genetic algorithm (GA) derived model (shown as FIG. 2C) involved Exemplar software. The GA options were set to: 1500 AND/OR models, of 15 iterations each, with a model size no larger than 5 (which permits 16 possible genotypes). Further details of the genetic algorithm implementation and significance testing are included as Example 2.

A Classification & Regression Tree Analysis was performed with the SPSS version 14.0 statistical package with the appropriate module on the Columbia, Iowa and combined data recoded as with (+) or without (−) minor alleles. Models were automatically generated using each of the three datasets that incorporated both CFH and C2/BF loci as contributors to the dependent outcome.

Results

All 18 BF exons, including 50-80 bp of flanking intronic regions, were analyzed initially by denaturing HPLC in approximately 90 AMD cases and 90 controls from a cohort ascertained at Columbia University. Seventeen sequence variants, including eight missense changes, were identified and the L9H (rs4151667) and R32Q (rs641153) alleles were more frequent in controls than in cases (Table 1). Haplotype-tagging SNPs (htSNPs) within BF and its adjacent homolog C2 were identified (FIG. 1) and genotyped in a Columbia University cohort comprised of 548 AMD cases and 275 controls. These analyses revealed four variants that were significantly associated with AMD. The L9H variant in BF, which was in nearly complete linkage disequilibrium (LD) with the E318D variant in C2 (rs9332739), was highly protective for AMD (X2=13.8 P=0.00020, OR=0.37 [95% CI=0.18-0.60]). The R32Q allele in BF was in nearly complete LD with the rs547154 SNP in intron 10 of C2, and was also highly protective (X2=33.7, P=$6.43 \times 10^{-9}$, OR=0.32 [95% CI=0.21-0.48]).

Genotyping of an independent cohort of 350 cases and 114 controls from the University of Iowa confirmed these findings. For example, the C2 E318D/BF L9H SNP pair was significantly associated with AMD in this cohort (X2=10.6, P=0.0012, OR=0.34 [95% CI=0.18-0.67]. To analyze haplotypes across the C2 and BF loci, the data from the two cohorts were combined (Table 2). The common haplotype (H1, FIG. 1) conferred a significant risk for AMD (X2=10.3, P=0.0013, OR=1.32 [95% CI=1.1–1.6]). The haplotype tagged by the BF R32Q SNP (H7), compared to all other haplotypes, was highly protective for AMD (X2=26.9, P=$2.1 \times 10^{-7}$, OR=0.45 [95% CI=0.33-0.61] and the C2 E318D/BF L9H-containing haplotype (H10) was also significantly protective (X2=21.6, P=$3.4 \times 10^{-6}$, OR=0.36 [95% CI=0.23-0.56]) (FIG. 1). The H1 haplotype, when employed as the reference haplotype, produced slightly more significant results for H7 (X2=29.6, OR=0.42 [0.32-0.58]) and for H10 (X2=24.9 OR=0.33 [0.21-0.52]). Analysis with the SNPEM program also demonstrated that the same haplotypes were significantly associated with the disease, confirming the hypothesis that alleles in the C2 and/or BF gene are predictive of risk for AMD. Individuals with the two protective haplotypes (either homozygous for H7, H10, or 7/10 compound heterozygotes) were found in 3.4% of the controls, but in only 0.77% of the cases (X2=12.2, P=0.00048, OR=0.22 [0.087-0.56]). The odds ratio of subjects with two protective alleles was approximately half of that of the subjects with one protective allele, consistent with a co-dominant model.

The observed associations were highly significant when the entire AMD subject cohort was compared to controls, or when major subtypes of AMD, including early AMD (eAMD), choroidal neovascularization (CNV) and geographic atrophy (GA), were analyzed separately. The GA group (a total of 133 subjects from the 2 cohorts) deviated from the general trend in some cases, similar to our observations related to CFH (Hageman et al., 2005, supra). Specifically, the haplotype tagged by the R32Q allele demonstrated the strongest protection against the disease—OR was 0.22 when the GA group was compared to controls vs. 0.45 when the rest of AMD samples were subjected to the same analysis. Although this deviation may be significant in terms of varying etiology of the disease, it did not reach statistical significance (the confidence intervals overlapped), most likely due to the small number of GA cases.

Combined analyses were initially performed by stratifying the subjects according to status at the CFH Y402H allele. Protection conferred by C2/BF was strongest in CFH 402H homozygotes (OR=0.27), intermediate in 402H/Y heterozygotes (OR=0.36), and weakest in 402Y homozygotes (OR=0.44). However, the confidence intervals of all these estimates overlapped. The effect was principally due to a trend in which the frequency of C2/BF protective alleles was greatest in 402H homozygotes (the "risk" genotype); 40% of these subjects in the control cohort carried at least one protective allele. In contrast, controls that were 402H/Y or 402Y had progressively lower frequencies of C2/BF protection (32% and 26% respectively). In other words, individuals at high risk due to their CFH genotype, who did not develop AMD, have a high frequency of protective allele(s) at the C2/BF locus.

To identify possible combinations of CFH and C2/BF SNPs that are protective for AMD, as suggested by the individual SNP analysis, the analyses of the available data was performed by two means; first by an empirical hand-built model and then by a machine-learned model using the Exemplar software (FIG. 2). The first model was a hypothesized (hand-built) model, as one would create by an empirical inspection of the data (FIG. 2A). The model description is provided as panel A, and is interpreted as giving four possible combinations of genotypes that would protect from AMD (combinations that result in the model being "true"). When this model was applied against the samples, the distributions shown in panel B were obtained separately for each cohort and for the combined cohorts (FIG. 2B). The case percentage is the percentage of cases for which the model was false; in other words, they did not have protection as described by the model. The control percentage is the percentage of controls that did have the protective factors described by the model, meaning the model was true. These distributions were subjected to significance testing by Fisher's exact test and evidenced p-values of P=0.00237, P=4.28×10−8 and P=7.90× 10−10, respectively. Following this, the Exemplar software was tasked to generate a protective model that provided a "best fit" to the data using a machine-learning method called Genetic Algorithms; i.e., we tested the hypothesis that the machine-learning software can outperform the hand-built model. Models were learned on the Columbia cohort; the resulting fittest models were retained and then applied to the Iowa cohort as a verification test (out-of-sample verification) on an independent cohort. Finally, the models were applied to the combined sample set. The resulting best performing model is depicted in FIG. 2C. This model describes four possible individual (or combinations of) genotypes that would protect from AMD (i.e. combinations resulting in the model being "true"). The model performance is shown in FIG. 2D for the Iowa, Columbia, and combined cohorts, respectively. These distributions were subjected to significance testing by Fisher's exact test and evidenced p-values of P=7.49×10$^{-5}$, P=2.97×10$^{-22}$ and P=1.69×10$^{-23}$, respectively. The method was further validated by randomizing the case and control designations and performing 3000 permutations of the dataset. The actual data was more significant than any of these permutations.

In summary, combined analysis of these haplotypes with the variation in CFH by the Exemplar software revealed that 56% of unaffected controls harbor at least one protective CFH or C2/BF haplotype, while 74% of AMD subjects lack any protective haplotype at these loci. Inspection of the data shows that approximately 60% of the risk in cases and 65% of the protection of controls is due to the effect of the CFH locus, and the remainder (40% and 35%, respectively) to the C2/BF locus. The machine-learned model outperformed the hand built model, allowing for significantly better predictions of a clinical outcome. A classification and regression tree (C&RT) analysis provided results that support the role of C2/BF in AMD, producing similar trees as did the Genetic Algorithm analysis. Using the Columbia dataset alone, the C&RT model accounts for 37% of cases through C2/BF allele presence, using Iowa, 36%, and the combined analysis produced a slightly weaker effect of 27%. These estimates are all consistent with the 35-40% estimated contribution of the C2/BF locus from the genetic algorithm analysis. The detailed description of the methods and specific analyses are provided in the Example 2.

Figures 3A, 3B, 3C:
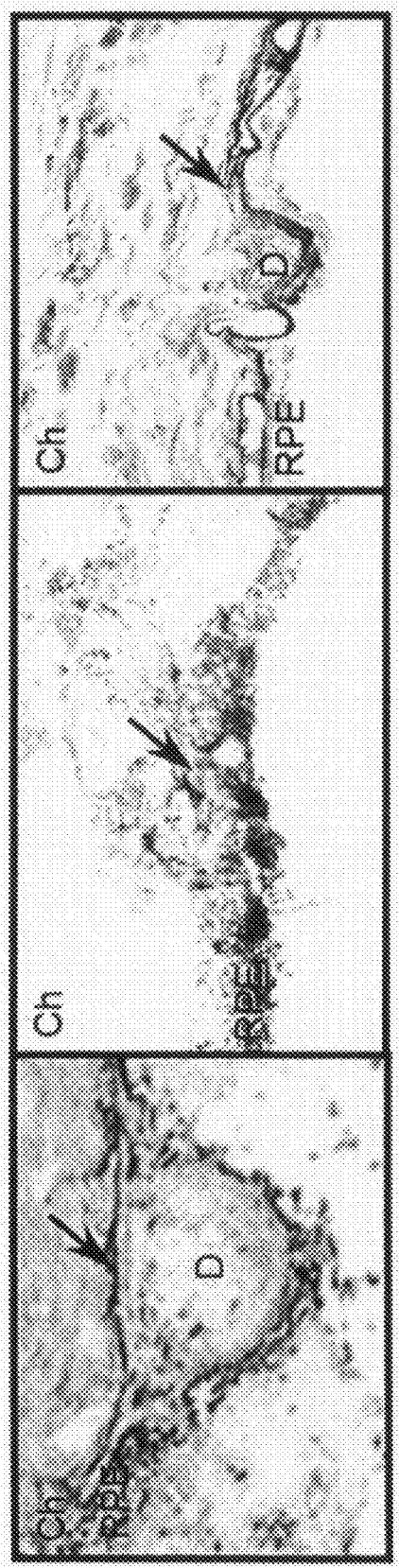
FIG. 3 shows immunolocalization of BF (FIG. 3A); Ba (a fragment of the full-length factor B) (FIG. 3B); and C3 (FIG. 3C) along the retinal pigment epithelium (RPE)-choroid (CH) complex in sections from an unfixed eye of a 72 year old donor with early stage AMD. Anti-BF antibody (Quidel; reaction product is red) labels drusen (D), particularly along their rims, Bruch's membrane, and the choroidal stroma. Anti-Ba antibody (Quidel; reaction product is purple) labels Bruch's membrane and RPE-associated patches. Note that the distribution of BF is similar to that of C3. Brown coloration in the RPE cytoplasm and choroid is due to melanin. Bruch's membrane (BM); Retina (R).

BF and C2 are expressed in the neural retina, RPE, and choroid. PCR amplicons of the appropriate sizes for BF and C2 gene products were detected from isolated RPE, the RPE/choroid complex, and the neural retina, from human donor eyes with (two donors aged 67 and 94) and without (two donors aged 69 and 82) AMD (data not shown). BF protein was present in ocular drusen, within Bruch's membrane, and less prominently in the choroidal stroma (FIG. 3A). Ba (a BF-derived peptide) immunoreactivity was less pronounced, but distinctly present in patches associated with RPE cells and throughout Bruch's membrane (FIG. 3B). The distribution of BF is similar to that of C3 (FIG. 3C), both of which are essentially identical to that of CFH and C5b-9 (Hageman et al., 2005, supra).

In summary, these data show that variants the complement pathway-associated genes C2 and BF are significantly associated with AMD. Protective haplotypes in the C2/BF locus contain nonsynonymous SNPs in the BF gene, an important activator of the alternative complement pathway. Available data confirms the hypothesis that the AMD phenotype may be modulated by abnormal BF activity. Indeed, the BF protein containing glutamine at position 32 (resulting from one of the two BF SNPs tagging a protective haplotype), has been shown to have reduced hemolytic activity compared to the more frequent arginine 32 form (Lokki and Koskimies (1991) *Immunogenetics* 34:242-6). The same study did not document a functional effect for the R32W variant, which was not associated with AMD in the current study. Based on these data, we suggest that an activator with reduced enzymatic activity provides a lower risk for chronic complement response that can lead to drusen formation and AMD. This hypothesis is compatible with our previous proposal that insufficient inhibition of the alternative complement cascade due to variation in CFH results in chronic damage at the retinal pigment epithelium/Bruch's membrane interface (Hageman et al., 2005, supra; Anderson, 2002, supra; Hageman, 2001, supra). Another BF htSNP, L9H, resides in the signal peptide. While the functional consequence of this variant has not been directly demonstrated, this variant could modulate BF secretion.

The genetic and functional data suggests that variation in BF is likely causal for the observed association with AMD. This is based on the fact that the two haplotype-tagging variants in BF are non-conservative and one of the two is documented to have a direct functional relevance (a reduced hemolytic activity), whereas the variants in C2 are a conservative change and an intronic SNP. In addition, BF participates directly in the alternative pathway, a pathway that also involves CFH. A direct role cannot be ruled out for C2, however, particularly since both C2 and BF regulate the production of C3. C2 and BF have nearly identical modular structures, including serine protease domains within their carboxy termini and three CCP modules within their amino termini. Additional support for BF being the gene involved in pathogenesis of AMD comes from studies of drusen composition. While the majority of proteins involved in the alternative pathway (CFH, BF, etc.) are found in drusen, their analogs from the classical pathway, such as C2 and C4, are not (Mullins et al. (2000) *Faseb J.* 14:835-46; Crabb et al. (2002) *Proc. Natl. Acad. Sci. U.S.A.* 99:14682-7). These data further suggest that the SNPs in C2 gene are associated with AMD due to extensive LD with BF.

Several common functional variants in both C2 and BF have been described (Davis and Forristal (1980) *J. Lab. Clin. Med.* 96:633-9; Raum et al. (1979) *Am. J. Hum. Genet.* 31:35-41.; Alper et al. (2003) *J. Clin. Immunol.* 23:297-305), but most of these are rare. All missense alleles with frequencies greater than 2% in European populations as judged from the re-sequencing data on both genes available at the SeattleSNPs project website (www.pga.mbt.washington.edu/) have been analyzed. Moreover, no additional nonsynonymous variants in either gene have been found after complete sequencing of several HLA haplotypes, including examples of our haplotypes H2, H5, and H7 (Stewart et al. (2004) *Genome Res.* 14:1176-87).

Because C2 and BF reside in the HLA locus together with many other genes involved in inflammation, one must consider the possibility that the associations observed in this study are due to LD with adjacent loci (Larsen and Alper (2004) *Curr. Opin. Immunol.* 16:660-7). Five lines of evidence, however, suggest that the C2/BF locus is the main contributor to the observed association. First, only modest LD between C2/BF and adjacent class III loci is observed in HapMap data. Second, MHC class II loci and BF haplotypes H7 and H10 do not show strong LD. Third, in a whole genome scan performed by Klein et al. (2005) *Science* 308:385-9, the MHC locus did not demonstrate a statistically significant association with AMD. Their analysis, performed with the Affymetrix Mapping 100K Array, included 80 SNPs across the MHC locus; however, the array did not contain any of the 8 SNPs typed in this study (https://www.affymetrix.com/analysis/netaffx/index.affx). Fourth, estimated recombination rates from HapMap data indicate regions of high recombination on both sides of the C2/BF locus (Myers et al. (2005) *Science* 310:321-324). Finally, the single published study on MHC in AMD demonstrates modest protection for the class I locus B*4001 (P=0.027) and the class II locus DRB1*1301 (P=0.009) (Goverdhan et al. (2005) *Invest. Ophthalmol. Vis. Sci.* 46:1726-34). Since the protective alleles identified in this study were associated with AMD at a substantially higher statistical significance it is very unlikely that the C2/BF association is due to LD with these and/or other loci in the MHC.

TABLE 1

Sequence variants in the BF gene detected by DHPLC screening.

| Exon | Nucleotide Changes | Amino Acid Changes | Allele Frequency in Cases | | | | Controls |
|---|---|---|---|---|---|---|---|
| | | | AMD Total | N | GA | E | |
| 1 | c.26 T > A | L9H | 18/1092 | 10/546 | 2/178 | 6/368 | 23/546 |
| 2 | c.94 C > T | R32W | 109/1096 | 52/546 | 20/182 | 37/368 | 55/550 |
| 2 | c.95 G > A | R32Q | 44/1096 | 21/546 | 4/182 | 19/368 | 61/550 |
| 3 | c.405 C > T | Y135Y | 1/184 | 1/184 | | | 0/184 |
| 4 | c.504 G > A | P168P | 4/184 | 4/184 | | | 6/184 |
| 4 | c.600 C > T | S200S | 0/184 | 0/184 | | | 2/184 |
| 5 | c.673 C > T | Y252Y | 2/184 | 2/184 | | | 5/184 |
| 5 | c.754 G > A | G252S | 7/184 | 7/184 | | | 6/184 |
| 6 | c.897 + 17C > A | | 2/184 | 2/184 | | | 1/184 |
| 8 | c.1137 C > T | R379R | 1/184 | 1/184 | | | 0/184 |
| 9 | c.1169 − 35T > A | | 1/184 | 1/184 | | | 0/184 |
| 12 | c.1598 A > G | K533R | 3/184 | 3/184 | | | 9/184 |
| 14 | c.1693 A > G | K565E | 9/182 | 9/182 | | | 4/184 |
| 14 | c.1697 A > C | E566A | 9/182 | 9/182 | | | 4/184 |
| 15 | c.1856 − 14C > T | | 13/182 | 13/182 | | | 21/184 |
| 15 | c.1933 G > A | V645I | 1/182 | 1/182 | | | 0/184 |
| 18 | c.*23 C > T | | 4/182 | 4/182 | | | 7/182 |

TABLE 2

Association analysis of C2/BF variants in combined Columbia and Iowa cohorts

| Gene | dbSNP# | Location | # Cases | # Controls | $X^2$ | P | OR | 95% CI |
|---|---|---|---|---|---|---|---|---|
| C2 | rs9332739 | E318D | 897 | 381 | 21.2 | 4.14E−06 | 0.36 | 0.23-0.56 |
| C2 | rs547154 | IVS 10 | 894 | 382 | 28.7 | 8.45E−08 | 0.44 | 0.33-0.60 |
| BF | rs4151667 | L9H | 903 | 383 | 21.3 | 3.93E−06 | 0.36 | 0.23-0.56 |
| BF | rs641153 | R32Q | 551 | 269 | 33.7 | 6.43E−09 | 0.32 | 0.21-0.48 |
| BF | rs1048709 | R150R | 892 | 381 | 0.12 | NS | | |
| BF | rs4151659 | K565E | 902 | 384 | 1.1 | NS | | |
| BF | rs2072633 | IVS 17 | 893 | 379 | 4.05 | 0.044 | 0.84 | 0.70-0.99 |

Example 2

Exemplar Statistical Methods

Sapio Sciences collaborated with the NCI to analyze genotyping data. The NCI provided ~1360 total samples with 10 bi-allelic SNP's genotyped. The data was presented to Sapio with numeric representations of alleles. A script was written to convert the data to Exemplar-friendly format, by converting the alleles to genotype numeric representations ("1 1" became "1" for AA, "1 2" became "2" for AB and "2 2" became "3" for BB, "0 0" was a nocall and was converted to "0") and to dedup the samples. The phenotype was age-related macular degeneration (AMD). There were several subclasses of AMD identified, but for this analysis the data was used as a whole to determine if there was a common genotype underlying the various AMD phenotypes.

Sapio Sciences utilized its Exemplar Genotyping Analysis Suite to analyze the supplied data. Exemplar performs several association based analyses for case-control studies. The modules utilized for the analysis were:

Genetic Algorithm Module (GA Module)—This module implements a machine learning approach to finding logical combinations of SNP's (models) based studies.

Association Study Module (AS Module)—This module calculates many useful statistics like Chi Square, Yates, Fisher Exact, Odds Ratio, Relative risk, Linkage Disequilibrium, D', r2 and Haplotype Estimates.

Exemplar typically finds models correlating with a phenotype. In other words, the models predict the factors contributing to getting the phenotype, not to protection from it, although protective factors can be inferred from the models. For example, if a model indicates that samples having . . . RS001 as BB OR RS001 as AB . . . correlate with having the phenotype, then it can be inferred that those with RS001 as AA are protected from the phenotype.

Exemplar models are logical combinations of SNP's. The models can be hand-built to test hypothesis, or the Genetic Algorithm can be utilized to attempt to find models with high utility. Genetic Algorithms are a machine learning method that excels at finding patterns within large data spaces. The GA utilizes the two-thirds, one-third, validation method. This is accomplished by randomly assigning ⅔ of the cases and controls to the training set. The GA then learns models on this training set. When it completes the learning phase, it applies the best performing models to the test set (the remaining ⅓ of data). The best performing models across test and training are returned to the user. In this study, even though only a small number of SNP's were being interrogated, the large number of samples made it difficult for a human to effectively discern patterns that would be applicable across all the data. For this reason, the GA was utilized to find more complex patterns with higher utility. The benefit of these types of models over traditional approaches is in their ability to incorporate multiple loci from across the genome in making a prediction. This enables one model to identify what is often a complex interaction of polymorphisms that correlate with outcomes.

This study was unique in that its focus was on finding models that were protective against AMD. As this deviates from the normal Exemplar approach of finding additive models, a change had to be made to the input data. By simply instructing Exemplar that the cases were controls, and vice versa, it would then learn models that demonstrated why a sample would not get the phenotype. In other words, it would be finding the combinations of SNP's that conferred protection.

Study Group information: Data was provided from two separate cohorts, the Iowa cohort and the Columbia cohort. The Columbia data was a larger group with about 830 total samples of which 560 were cases and 270 were controls. The Iowa cohort had about 529 total samples with 414 cases and 115 controls. Having two sample groups allowed model building to be done with the GA Module on one cohort and the efficacy of the resultant models out-of-sample to be tested on the remaining cohort.

Study Results: Multiple statistics were generated for each SNP/genotype in the input dataset. Statistics were generated by building 2×2 contingency tables and doing proper counts of genotypes (Note that this is not allele counts, but genotype counts where the two genotypes not being calculated are collapsed into one value). The values for each cell of the 2×2 table are provided in the tables under the headings Case True, Case False, Control True, Control False. All statistics were two-tailed calculations.

Tables 3 through 6 show statistics on the Iowa and Columbia cohort side by side. NOTE: The "Category" column is the genotype where: 1 corresponds to AA, 2 to AB and 3 to BB. Table 7 shows statistics for the combined cohorts.

TABLE 3

Columbia and Iowa Side-By-Side Chi Square Statistics

| | Columbia - Chi Square | | | | | | Iowa - Chi Square | | | | | |
|---|---|---|---|---|---|---|---|---|---|---|---|---|
| SNP | Category | Score | Case True | Case False | Control True | Control False | SNP | Category | Score | Case True | Case False | Control True | Control False |
| RS1061147 | 3 | 58.05 | 110 | 433 | 121 | 141 | RS1061170 | 3 | 34.46 | 64 | 287 | 52 | 62 |
| RS1061170 | 3 | 53.45 | 114 | 432 | 120 | 142 | RS1061147 | 3 | 33.75 | 65 | 287 | 52 | 62 |
| RS1061147 | 1 | 34.82 | 160 | 383 | 28 | 234 | RS1061170 | 1 | 23.27 | 127 | 224 | 14 | 100 |
| RS1061170 | 1 | 26.19 | 158 | 388 | 33 | 229 | RS1061147 | 1 | 23.11 | 127 | 225 | 14 | 100 |
| RS547154 | 1 | 25.84 | 501 | 47 | 212 | 57 | INDELTT | 3 | 12.22 | 268 | 70 | 69 | 41 |
| RS547154 | 2 | 20.63 | 43 | 505 | 50 | 219 | RS9332739 | 1 | 9.31 | 334 | 19 | 98 | 16 |
| INDELTT | 3 | 20.56 | 413 | 143 | 158 | 111 | RS4151667 | 1 | 8.59 | 335 | 20 | 98 | 16 |
| INDELTT | 1 | 18.21 | 7 | 549 | 18 | 251 | INDELTT | 1 | 8.29 | 6 | 332 | 8 | 102 |
| RS4151667 | 1 | 11.85 | 532 | 18 | 245 | 24 | RS9332739 | 2 | 7.72 | 19 | 334 | 15 | 99 |
| RS2072633 | 3 | 11.61 | 56 | 485 | 51 | 218 | RS4151667 | 2 | 7.07 | 20 | 335 | 15 | 99 |
| RS9332739 | 1 | 10.86 | 527 | 19 | 243 | 24 | INDELTT | 2 | 5.99 | 64 | 274 | 33 | 77 |
| RS4156687 | 2 | 10.58 | 18 | 532 | 23 | 246 | RS547154 | 1 | 2.49 | 304 | 44 | 92 | 21 |
| RS9332739 | 2 | 9.65 | 19 | 527 | 23 | 244 | RS547154 | 2 | 2.06 | 43 | 305 | 20 | 93 |
| INDELTT | 2 | 9.24 | 136 | 420 | 93 | 176 | RS1048709 | 2 | 1.86 | 103 | 250 | 41 | 73 |
| RS1061170 | 2 | 5.23 | 274 | 272 | 109 | 153 | RS1061170 | 2 | 0.42 | 160 | 191 | 48 | 66 |
| RS1061147 | 2 | 3.62 | 273 | 270 | 113 | 149 | RS1061147 | 2 | 0.39 | 160 | 192 | 48 | 66 |
| RS3753396 | 3 | 3.48 | 8 | 541 | 9 | 250 | RS1048709 | 1 | 0.31 | 230 | 123 | 71 | 43 |
| RS2072633 | 1 | 1.66 | 245 | 296 | 109 | 160 | RS3753396 | 1 | 0.15 | 258 | 94 | 80 | 32 |
| RS3753396 | 1 | 1.61 | 403 | 146 | 179 | 80 | RS2072633 | 1 | 0.08 | 121 | 233 | 36 | 74 |
| RS2072633 | 2 | 1.08 | 240 | 301 | 109 | 160 | | | | | | | |
| RS4151659 | 2 | 0.22 | 22 | 527 | 9 | 260 | | | | | | | |
| RS1048709 | 1 | 0.02 | 412 | 129 | 202 | 65 | | | | | | | |

TABLE 4

Columbia and Iowa Side-By-Side Chi Square Yates Statistics

| | Columbia Chi - Square Yates | | | | | | Iowa - Chi Square Yates | | | | | |
|---|---|---|---|---|---|---|---|---|---|---|---|---|
| SNP | Category | Score | Case True | Case False | Control True | Control False | SNP | Category | Score | Case True | Case False | Control True | Control False |
| RS1061147 | 3 | 56.79 | 110 | 433 | 121 | 141 | RS1061170 | 3 | 33.01 | 64 | 287 | 52 | 62 |
| RS1061170 | 3 | 52.25 | 114 | 432 | 120 | 142 | RS1061147 | 3 | 32.32 | 65 | 287 | 52 | 62 |
| RS1061147 | 1 | 33.78 | 160 | 383 | 28 | 234 | RS1061170 | 1 | 22.15 | 127 | 224 | 14 | 100 |
| RS1061170 | 1 | 25.30 | 158 | 388 | 33 | 229 | RS1061147 | 1 | 22.00 | 127 | 225 | 14 | 100 |
| RS547154 | 1 | 24.72 | 501 | 47 | 212 | 57 | INDELTT | 3 | 11.34 | 268 | 70 | 69 | 41 |
| INDELTT | 3 | 19.63 | 413 | 143 | 158 | 111 | RS9332739 | 1 | 8.10 | 334 | 19 | 98 | 16 |
| RS547154 | 2 | 19.58 | 43 | 505 | 50 | 219 | RS4151667 | 1 | 7.45 | 335 | 20 | 98 | 16 |
| INDELTT | 1 | 16.41 | 7 | 549 | 18 | 251 | RS9332739 | 2 | 6.61 | 19 | 334 | 15 | 99 |
| RS2072633 | 3 | 10.87 | 56 | 485 | 51 | 218 | INDELTT | 1 | 6.57 | 6 | 332 | 8 | 102 |
| RS4151667 | 1 | 10.72 | 532 | 18 | 245 | 24 | RS4151667 | 2 | 6.03 | 20 | 335 | 15 | 99 |
| RS9332739 | 1 | 9.79 | 527 | 19 | 243 | 24 | INDELTT | 2 | 5.36 | 64 | 274 | 33 | 77 |
| RS4151667 | 2 | 9.50 | 18 | 532 | 23 | 246 | RS1048709 | 3 | 2.13 | 20 | 333 | 2 | 112 |
| INDELTT | 2 | 8.75 | 136 | 420 | 93 | 176 | RS547154 | 1 | 2.02 | 304 | 44 | 92 | 21 |
| RS9332739 | 2 | 8.63 | 19 | 527 | 23 | 244 | RS547154 | 2 | 1.64 | 43 | 305 | 20 | 93 |
| RS1061170 | 2 | 4.89 | 274 | 272 | 109 | 153 | RS1048709 | 2 | 1.56 | 103 | 250 | 41 | 73 |
| RS547154 | 3 | 3.46 | 4 | 544 | 7 | 262 | RS4151659 | 1 | 1.21 | 343 | 12 | 114 | 1 |
| RS1061147 | 2 | 3.34 | 273 | 270 | 113 | 149 | RS4151659 | 2 | 1.21 | 12 | 343 | 1 | 114 |
| RS3753396 | 3 | 2.57 | 8 | 541 | 9 | 250 | RS1061170 | 2 | 0.29 | 160 | 191 | 48 | 66 |
| RS2072633 | 1 | 1.47 | 245 | 296 | 109 | 160 | RS1061147 | 2 | 0.27 | 160 | 192 | 48 | 66 |
| RS3753396 | 1 | 1.40 | 403 | 146 | 179 | 80 | RS1048709 | 1 | 0.20 | 230 | 123 | 71 | 43 |
| RS2072633 | 2 | 0.93 | 240 | 301 | 109 | 160 | RS3753396 | 1 | 0.07 | 258 | 94 | 80 | 32 |
| RS4151659 | 2 | 0.07 | 22 | 527 | 9 | 260 | RS2072633 | 1 | 0.03 | 121 | 233 | 36 | 74 |
| RS1048709 | 1 | 0.00 | 412 | 129 | 202 | 65 | RS1061170 | 3 | 33.01 | 64 | 287 | 52 | 62 |

TABLE 5

Columbia and Iowa Side-By-Side Fishers Exact Statistics

| | Columbia - Fishers Exact | | | | | | Iowa - Fishers Exact | | | | | |
|---|---|---|---|---|---|---|---|---|---|---|---|---|
| SNP | Category | p-Value | Case True | Case False | Control True | Control False | SNP | Category | p-Value | Case True | Case False | Control True | Control False |
| RS1061147 | 3 | 1.11E−13 | 110 | 433 | 121 | 141 | RS1061170 | 3 | 1.56E−08 | 64 | 287 | 52 | 62 |
| RS1061170 | 3 | 5.32E−13 | 114 | 432 | 120 | 142 | RS1061147 | 3 | 2.13E−08 | 65 | 287 | 52 | 62 |
| RS1061147 | 1 | 5.33E−10 | 160 | 383 | 28 | 234 | RS1061170 | 1 | 3.23E−07 | 127 | 224 | 14 | 100 |

TABLE 5-continued

Columbia and Iowa Side-By-Side Fishers Exact Statistics

| Columbia - Fishers Exact | | | | | | | Iowa - Fishers Exact | | | | | | |
|---|---|---|---|---|---|---|---|---|---|---|---|---|---|
| SNP | Category | p-Value | Case True | Case False | Control True | Control False | SNP | Category | p-Value | Case True | Case False | Control True | Control False |
| RS1061170 | 1 | 8.67E−08 | 158 | 388 | 33 | 229 | RS1061147 | 1 | 3.52E−07 | 127 | 225 | 14 | 100 |
| RS547154 | 1 | 6.79E−07 | 501 | 47 | 212 | 57 | INDELTT | 3 | 5.12E−04 | 268 | 70 | 69 | 41 |
| INDELTT | 3 | 5.28E−06 | 413 | 143 | 158 | 111 | RS9332739 | 1 | 0.0034399 | 334 | 19 | 98 | 16 |
| RS547154 | 2 | 8.45E−06 | 43 | 505 | 50 | 219 | RS4151667 | 1 | 0.0046824 | 335 | 20 | 98 | 16 |
| INDELTT | 1 | 4.89E−05 | 7 | 649 | 18 | 251 | RS9332739 | 2 | 0.0070934 | 19 | 334 | 15 | 99 |
| RS2072633 | 3 | 6.15E−04 | 56 | 485 | 51 | 218 | INDELTT | 1 | 0.0082008 | 6 | 332 | 8 | 102 |
| RS4151667 | 1 | 7.59E−04 | 532 | 18 | 245 | 24 | RS4151667 | 2 | 0.0094281 | 20 | 335 | 15 | 99 |
| RS9332739 | 1 | 0.001202 | 527 | 19 | 243 | 24 | INDELTT | 2 | 0.0116306 | 64 | 274 | 33 | 77 |
| RS4151667 | 2 | 0.001399 | 18 | 532 | 23 | 246 | RS1048709 | 3 | 0.0636773 | 20 | 333 | 2 | 112 |
| INDELTT | 2 | 0.001690 | 136 | 420 | 93 | 176 | RS547154 | 1 | 0.0800174 | 304 | 44 | 92 | 21 |
| RS9332739 | 2 | 0.002166 | 19 | 527 | 23 | 244 | RS547154 | 2 | 0.1022408 | 43 | 305 | 20 | 93 |
| RS1061170 | 2 | 0.013402 | 274 | 272 | 109 | 153 | RS1048709 | 2 | 0.1067809 | 103 | 250 | 41 | 73 |
| RS1061147 | 2 | 0.033779 | 273 | 270 | 113 | 149 | RS4151659 | 1 | 0.1321014 | 343 | 12 | 114 | 1 |
| RS547154 | 3 | 0.035149 | 4 | 544 | 7 | 262 | RS4151659 | 2 | 0.1321014 | 12 | 343 | 1 | 114 |
| RS3753396 | 3 | 0.058108 | 8 | 541 | 9 | 250 | RS4151667 | 3 | 0.2430704 | 0 | 355 | 1 | 113 |
| RS2072633 | 1 | 0.112503 | 245 | 296 | 109 | 160 | RS9332739 | 3 | 0.2441113 | 0 | 353 | 1 | 113 |
| RS3753396 | 1 | 0.118293 | 403 | 146 | 179 | 80 | RS1061170 | 2 | 0.2949213 | 160 | 191 | 48 | 66 |
| RS2072633 | 2 | 0.167401 | 240 | 301 | 109 | 160 | RS1061147 | 2 | 0.3032103 | 160 | 192 | 48 | 66 |
| RS9332739 | 3 | 0.328413 | 0 | 546 | 1 | 266 | RS1048709 | 1 | 0.3265887 | 230 | 123 | 71 | 43 |
| RS4151667 | 3 | 0.328449 | 0 | 550 | 1 | 268 | RS3753396 | 1 | 0.3921321 | 258 | 94 | 80 | 32 |
| RS4151659 | 2 | 0.401117 | 22 | 527 | 9 | 260 | RS2072633 | 1 | 0.4366061 | 121 | 233 | 36 | 74 |
| RS1048709 | 1 | 0.470495 | 412 | 129 | 202 | 65 | RS1061170 | 3 | 1.56E−08 | 64 | 287 | 52 | 62 |

TABLE 6

Columbia and Iowa Side-By-Side Odds Ratio Statistics

| Columbia-Odds Ratio | | | | | | | Iowa-Odds Ratio | | | | | | |
|---|---|---|---|---|---|---|---|---|---|---|---|---|---|
| SNP | Category | Score | Case True | Case False | Control True | Control False | SNP | Category | Score | Case True | Case False | Control True | Control False |
| RS1061147 | 1 | 3.491 | 160 | 383 | 28 | 234 | RS1061170 | 1 | 4.050 | 127 | 224 | 14 | 100 |
| RS4151667 | 1 | 2.895 | 532 | 18 | 245 | 24 | RS1061147 | 1 | 4.032 | 127 | 225 | 14 | 100 |
|  |  |  | 501 | 47 | 212 | 57 | RS4151659 | 2 | 3.988 | 12 | 343 | 1 | 114 |
| RS1061170 | 1 | 2.826 | 158 | 388 | 33 | 229 | RS1048709 | 3 | 3.363 | 20 | 333 | 2 | 112 |
| RS9332739 | 1 | 2.739 | 527 | 19 | 243 | 24 | RS9332739 | 1 | 2.870 | 334 | 19 | 98 | 16 |
| INDELTT | 3 | 2.029 | 413 | 143 | 158 | 111 | RS4151667 | 1 | 2.735 | 335 | 20 | 98 | 16 |
| RS1061170 | 2 | 1.414 | 274 | 272 | 109 | 153 | INDELTT | 3 | 2.275 | 268 | 70 | 69 | 41 |
| RS1061147 | 2 | 1.333 | 273 | 270 | 113 | 149 |  |  |  | 304 | 44 | 92 | 21 |
| RS3753396 | 1 | 1.234 | 403 | 146 | 179 | 80 | RS1061170 | 2 | 1.152 | 160 | 191 | 48 | 66 |
| RS2072633 | 1 | 1.215 | 245 | 296 | 109 | 160 | RS1061147 | 2 | 1.146 | 160 | 192 | 48 | 66 |
| RS4151659 | 2 | 1.206 | 22 | 527 | 9 | 260 | RS1048709 | 1 | 1.132 | 230 | 123 | 71 | 43 |
| RS2072633 | 2 | 1.170 | 240 | 301 | 109 | 160 | RS3753396 | 1 | 1.098 | 258 | 94 | 80 | 32 |
| RS1048709 | 1 | 1.028 | 412 | 129 | 202 | 65 | RS2072633 | 1 | 1.067 | 121 | 233 | 36 | 74 |
| RS1048709 | 2 | 1.005 | 122 | 419 | 60 | 207 | RS1048709 | 2 | 0.734 | 103 | 250 | 41 | 73 |
| INDELTT | 2 | 0.613 | 136 | 420 | 93 | 176 | RS547154 | 2 | 0.656 | 43 | 305 | 20 | 93 |
| RS2072633 | 3 | 0.494 | 56 | 485 | 51 | 218 | INDELTT | 2 | 0.545 | 64 | 274 | 33 | 77 |
| RS3753395 | 3 | 0.411 | 8 | 541 | 9 | 250 | RS4151667 | 2 | 0.394 | 20 | 335 | 15 | 99 |
| RS9332739 | 2 | 0.382 | 19 | 527 | 23 | 244 | RS9332739 | 2 | 0.375 | 19 | 334 | 15 | 99 |
| RS547154 | 2 | 0.373 | 43 | 505 | 50 | 219 | RS1061147 | 3 | 0.270 | 65 | 287 | 52 | 62 |
| RS4151667 | 2 | 0.362 | 18 | 532 | 23 | 246 | RS1061170 | 3 | 0.266 | 64 | 287 | 52 | 62 |
| RS1061170 | 3 | 0.312 | 114 | 432 | 120 | 142 | RS4151659 | 1 | 0.251 | 343 | 12 | 114 | 1 |
| RS1061147 | 3 | 0.296 | 110 | 433 | 121 | 141 | INDELTT | 1 | 0.230 | 6 | 332 | 8 | 102 |
| RS547154 | 3 | 0.275 | 4 | 544 | 7 | 262 |  |  |  |  |  |  |  |
| INDELTT | 1 | 0.178 | 7 | 549 | 18 | 251 |  |  |  |  |  |  |  |

TABLE 7

Combined Cohorts Chi Square Statistics
Combined Cohorts - Chi Square

| SNP | Category | Score | Case True | Case False | Control True | Control False |
|---|---|---|---|---|---|---|
| RS1061170 | 3 | 89.16 | 178 | 719 | 172 | 204 |
| RS1061170 | 1 | 51.05 | 285 | 612 | 47 | 329 |
| INDELTT | 3 | 34.49 | 681 | 213 | 227 | 152 |
| INDELTT | 1 | 26.19 | 13 | 881 | 26 | 353 |
| RS547154 | 1 | 24.58 | 805 | 91 | 304 | 78 |
| RS547154 | 2 | 19.03 | 86 | 810 | 70 | 312 |
| RS4151667 | 1 | 18.45 | 867 | 38 | 343 | 40 |
| RS9332739 | 1 | 18.39 | 861 | 38 | 341 | 40 |
| INDELTT | 2 | 16.52 | 200 | 694 | 126 | 253 |
| RS4151667 | 2 | 15.87 | 38 | 867 | 38 | 345 |
| RS9332739 | 2 | 15.82 | 38 | 861 | 38 | 343 |
| RS2072633 | 3 | 7.39 | 113 | 782 | 70 | 309 |
| RS547154 | 3 | 6.28 | 5 | 891 | 8 | 374 |
| RS1061170 | 2 | 4.68 | 434 | 463 | 157 | 219 |
| RS3753396 | 3 | 4.13 | 15 | 886 | 13 | 358 |
| RS1061147 | 2 | 3.29 | 433 | 462 | 161 | 215 |
| RS3753396 | 1 | 1.66 | 661 | 240 | 259 | 112 |
| RS1048709 | 3 | 1.44 | 27 | 867 | 7 | 374 |
| RS2072633 | 2 | 1.11 | 416 | 479 | 164 | 215 |
| RS4151659 | 1 | 1.09 | 870 | 34 | 374 | 10 |
| RS4151659 | 2 | 1.09 | 34 | 870 | 10 | 374 |
| RS2072633 | 1 | 0.77 | 366 | 529 | 145 | 234 |

TABLE 8

Combined Cohorts Chi Square Yates Statistics
Combined Cohorts - Chi Square Yates

| SNP | Category | Score | Case True | Case False | Control True | Control False |
|---|---|---|---|---|---|---|
| RS1061170 | 3 | 87.86 | 178 | 719 | 172 | 204 |
| RS1061170 | 1 | 50.05 | 285 | 612 | 47 | 329 |
| INDELTT | 3 | 33.70 | 681 | 213 | 227 | 152 |
| INDELTT | 1 | 24.40 | 13 | 881 | 26 | 353 |
| RS547154 | 1 | 23.69 | 805 | 91 | 304 | 78 |
| RS547154 | 2 | 18.23 | 86 | 810 | 70 | 312 |
| RS4151667 | 1 | 17.37 | 867 | 38 | 343 | 40 |
| RS9332739 | 1 | 17.31 | 861 | 38 | 341 | 40 |
| INDELTT | 2 | 15.95 | 200 | 694 | 126 | 253 |
| RS4151667 | 2 | 14.86 | 38 | 867 | 38 | 345 |
| RS9332739 | 2 | 14.81 | 38 | 861 | 38 | 343 |
| RS2072633 | 3 | 6.92 | 113 | 782 | 70 | 309 |
| RS547154 | 3 | 4.84 | 5 | 891 | 8 | 374 |
| RS1061170 | 2 | 4.42 | 434 | 463 | 157 | 219 |
| RS3753396 | 3 | 3.32 | 15 | 886 | 13 | 358 |
| RS1061147 | 2 | 3.07 | 433 | 462 | 161 | 215 |
| RS3753396 | 1 | 1.48 | 661 | 240 | 259 | 112 |
| RS1048709 | 3 | 1.02 | 27 | 867 | 1 | 374 |
| RS2072633 | 2 | 0.98 | 416 | 479 | 164 | 215 |
| RS4151659 | 1 | 0.77 | 870 | 34 | 374 | 10 |
| RS4151659 | 2 | 0.77 | 34 | 870 | 10 | 374 |
| RS2072633 | 1 | 0.66 | 366 | 529 | 145 | 234 |

TABLE 9

Combined Cohorts Fishers Exact Statistic
Combined Cohorts - Fishers Exact

| SNP | Category | p-Value | Case True | Case False | Control True | Control False |
|---|---|---|---|---|---|---|
| RS1061170 | 3 | 4.81E−20 | 178 | 719 | 172 | 204 |
| RS1061170 | 1 | 1.08E−13 | 285 | 612 | 47 | 329 |
| INDELTT | 3 | 5.56E−09 | 681 | 213 | 227 | 152 |
| RS547154 | 1 | 1.17E−06 | 805 | 91 | 304 | 78 |
| INDELTT | 1 | 1.45E−06 | 13 | 881 | 26 | 353 |
| RS547154 | 2 | 1.68E−05 | 86 | 810 | 70 | 312 |
| RS4151667 | 1 | 3.14E−05 | 867 | 38 | 343 | 40 |
| RS9332739 | 1 | 3.21E−05 | 861 | 38 | 341 | 40 |
| INDELTT | 2 | 4.10E−05 | 200 | 694 | 126 | 253 |
| RS4151667 | 2 | 1.04E−04 | 38 | 867 | 38 | 345 |
| RS9332739 | 2 | 1.06E−04 | 38 | 861 | 38 | 343 |
| RS2072633 | 3 | 0.0048033 | 113 | 782 | 70 | 309 |
| RS547154 | 3 | 0.0173168 | 5 | 891 | 8 | 374 |
| RS1061170 | 2 | 0.0176623 | 434 | 463 | 157 | 219 |
| RS3753396 | 3 | 0.0379421 | 15 | 886 | 13 | 358 |
| RS1061147 | 2 | 0.0397575 | 433 | 462 | 161 | 215 |
| RS4151667 | 3 | 0.0882608 | 0 | 905 | 2 | 381 |

TABLE 10

Combined Cohorts Odds Ratio Statistics
Combined Cohorts - Odds Ratio

| SNP | Category | Score | Case True | Case False | Control True | Control False |
|---|---|---|---|---|---|---|
| RS1061170 | 1 | 3.260 | 285 | 612 | 47 | 329 |
| RS4151667 | 1 | 2.661 | 867 | 38 | 343 | 40 |
| RS9332739 | 1 | 2.658 | 861 | 38 | 341 | 40 |
| RS547154 | 1 | 2.270 | 805 | 91 | 304 | 78 |
| INDELTT | 3 | 2.141 | 681 | 213 | 227 | 152 |
| RS1048709 | 3 | 1.664 | 27 | 867 | 7 | 374 |
| RS4151659 | 2 | 1.462 | 34 | 870 | 10 | 374 |
| RS1061170 | 2 | 1.308 | 434 | 463 | 157 | 219 |
| RS1061147 | 2 | 1.252 | 433 | 462 | 161 | 215 |
| RS3753396 | 1 | 1.191 | 661 | 240 | 259 | 112 |
| RS2072633 | 2 | 1.139 | 416 | 479 | 164 | 215 |
| RS2072633 | 1 | 1.117 | 366 | 529 | 145 | 234 |
| RS1048709 | 1 | 1.008 | 642 | 252 | 273 | 108 |
| RS4151659 | 1 | 0.684 | 870 | 34 | 374 | 10 |
| RS2072633 | 3 | 0.638 | 113 | 782 | 70 | 309 |
| INDELTT | 2 | 0.579 | 200 | 694 | 126 | 253 |
| RS547154 | 2 | 0.473 | 86 | 810 | 70 | 312 |
| RS3753396 | 3 | 0.466 | 15 | 886 | 13 | 358 |
| RS9332739 | 2 | 0.398 | 38 | 861 | 38 | 343 |
| RS4151667 | 2 | 0.398 | 38 | 867 | 38 | 345 |
| RS1061170 | 3 | 0.294 | 178 | 719 | 172 | 204 |
| RS547154 | 3 | 0.262 | 5 | 891 | 8 | 374 |
| INDELTT | 1 | 0.200 | 13 | 881 | 26 | 353 |
| RS1061170 | 1 | 3.260 | 285 | 612 | 47 | 329 |

Clearly many of these SNP's were highly statistically significant in both cohorts. This was mainly due to the a priori information that led to their selection for this study. Particularly notable was RS1061170 as 3(BB a.k.a T/T) with fishers p<4.81E-20, indicating its strong potential as a protective genotype. In the side by side comparisons it becomes clear that there are some differences between the Iowa and Columbia cohorts.

To further assess which SNP's/Genotypes are protective or contributive, Fishers was used as a basis for genotype penetration variance. To do this the genotype percentage was calculated for cases and controls and the absolute value of their difference was calculated. Table 11 provides this information and is sorted in order of highest frequency difference.

TABLE 11

Genotype Penetration Variance

| SNP | Genotype | Case % | Control % | Difference | Causative/Protective |
|---|---|---|---|---|---|
| RS1061170 | 3 | 19.84% | 45.74% | 25.90% | P |
| RS1061170 | 1 | 31.77% | 12.50% | 19.27% | C |

TABLE 11-continued

Genotype Penetration Variance

| SNP | Genotype | Case % | Control % | Difference | Causative/ Protective |
|---|---|---|---|---|---|
| INDELTT | 3 | 76.17% | 59.89% | 16.28% | C |
| INDELTT | 2 | 22.37% | 33.25% | 10.87% | P |
| RS547154 | 1 | 89.84% | 79.58% | 10.26% | C |
| RS547154 | 2 | 9.60% | 18.32% | 8.73% | P |
| RS1061170 | 2 | 48.38% | 41.76% | 6.63% | C |
| RS9332739 | 1 | 95.77% | 89.50% | 6.27% | C |

TABLE 11-continued

Genotype Penetration Variance

| SNP | Genotype | Case % | Control % | Difference | Causative/ Protective |
|---|---|---|---|---|---|
| RS4151667 | 1 | 95.80% | 89.56% | 6.24% | C |
| RS2072633 | 3 | 12.63% | 18.47% | 5.84% | P |
| RS9332739 | 2 | 4.23% | 9.97% | 5.75% | P |
| RS4151667 | 2 | 4.20% | 9.92% | 5.72% | P |
| RS1061147 | 2 | 48.38% | 42.82% | 5.56% | C |
| INDELTT | 1 | 1.45% | 6.86% | 5.41% | P |

Hypothesized Protective Models: In this study, preliminary work indicated possible combinations of SNP's that would protect from AMD. To test this hypothesis, a hand-built model was constructed per an NCI specification. The model graphic appears in FIG. 2A. This model can be written as an IF statement as follows:
 IF RS547154 is G/A and RS1061170 is T/T or
 RS547154 is G/A and RS1061170 is C/C or
 RS4151667 is T/A and RS1061170 is C/T or
 RS4151667 is T/A and RS1061170 is C/C
 THEN The Person is protected from AMD.
Therefore, this model gives four possible combinations of genotypes that would protect from AMD (combinations that result in the model being "true"):
 1. RS547154 as G/A AND RS1061170 as T/T
    Controls 8.82%, Cases 5.45%
 2. RS547154 as G/A AND RS1061170 as C/C
    Controls 7.22%, Cases 1.93%
 3. RS4151667 as T/A AND RS1061170 as C/T
    Controls 4.8%, Cases 2.02%
 4. RS4151667 as T/A AND RS1061170 as C/C
    Controls 3.47%, Cases 0.79%
When this model was applied against the samples, the following resulted for the combined Iowa and Columbia cohorts:
 794 cases did not have the protective factors (the model was false) . . . 90.12%
 88 controls did have the protective factors (the model was true) . . . 23.52%
 87 of the cases did have protective factors . . . 9.88%
 286 of the controls did not have the protective factors . . . 76.47

NOTE: statistics on all models were calculated by applying the model against the combined cohorts and tracking its True Positive(TP), False Negative(FN), False Positive(FP) and True Negative(TN) rates. These numbers were then placed in a 2×2 tables from which all statistics were generated. Table 12 shows the statistics for each cohort.

TABLE 12

NCI Hypothesized Protective Model Statistics

| | Iowa & Columbia | | Columbia | | Iowa | |
|---|---|---|---|---|---|---|
| | Score | Value | Score | Value | Score | Value |
| Fishers | | P = 7.902e−10 | | P = 4.284e−8 | | P = 0.00237 |
| Odds Ratio | | 2.8081 Std Error: 0.4666 95% CI: 2.027 < O.R. < 3.889 Inverse OR: .36 | | 3.2703 | | 2.3608 |
| Chi Square | 40.791 | P = 4.473E−11 | 32.928 | P = 9.563E−9 | 10.276 | P = 0.0013 |
| Yates | 39.661 | P = 3.020E−10 | 31.659 | P = 1.837E−8 | 9.334 | P = 0.0022 |

Genetic Algorithm (GA) Derived Model(s): In an attempt to see if the GA Module could find better combinations of SNP's, the GA module was tasked to learn models on the inverted data (to learn protective models). Various parameter settings were utilized including:
 Model Type: indicates whether the model can have and's and or's, and's only, or or's only.
 Model Size: indicates an upper limit for how many SNP's can be in the models
 GA Specific Parameters: such as generations, number of models, etc.
 Generally speaking, AND-only models of small size are preferable. The reasons for this are two-fold. First, an AND-only model requires that all its SNP's be true for the model to be true, and its interpretation is therefore unambiguous, whereas models with OR's do not require all SNP's to be present for the model to be true, which introduces a level of uncertainty. Secondly, smaller models are easier to interpret due to having fewer SNP's to assess.
 Exemplar utilizes a two-third, one-third validation method to avoid over-fitting to the input data with the desired outcome of having more generally applicable results.
 Further, given that there were two distinct study groups, this allowed models to be built only on the Columbia data and the resultant models to be tested against the Iowa cohort. If the model(s) performance is consistent across the two groups, this is a strong indication of the general applicability of the model(s). This would be particularly challenging given the interesting statistical differences between the two groups as discussed in the above statistics section. Given such variance, it was highly possible that the GA would find high fitness models on the Columbia data, but would perform poorly on the Iowa data.
 The GA did find a model that performed well across Columbia, Iowa and the combined dataset. The models performance on the Columbia data was superior to the Iowa data, as would be expected given that the model was trained on the Columbia data. Nonetheless, the model performance is notable given that the GA had no prior knowledge of the Iowa data and there was significant statistical difference between key SNP's between the two cohorts. The resultant best model outperformed the hand built hypothesized model on the combined cohorts (RS1061170). Initially, the model included an additional section with "INDELTT is homozygous AND RS547154 is GG," but upon further inspection, this section was determined to be extraneous to model interpretation and was therefore eliminated to produce the model with identical performance. A graphic of the final model may be found in FIG. 2C.

The GA specific Options for this task were as follows:
Models: 1500—this is the number of models the GA built internally as a foundation for evolving new generations of models
Iterations: 25—this is the number of evolutionary iterations the models went through to find a solution
Model Size: 5—this allowed for the models to have a maximum of 16 genotypes to appear in a single model
Model Type: AND/OR's—this let the GA build models that could use both and's and or's This model can be written as an IF statement as follows:
IF RS1048709 is G/G and RS1061170 is T/T or
RS547154 is G/A or
RS4151667 is T/A or
INDELTT is +/+
THEN The person is protected from AMD.

This model gives four possible individual or combinations of genotypes that would protect from AMD (combinations resulting in the model being "true"):
1. RS1048709 as G/G and RS1061170 as T/T
   Occurred in 14.20% cases, 34.31% controls
2. RS547154 as G/A
   Occurred in 9.6% cases, 18.32% controls
3. RS4151667 as T/A
   Occurred in 4.2% cases, 9.92% controls
4. INDELTT as +/+
   Occurred in 1.45% cases, 6.86% controls When this model was applied against the samples, the following resulted for the combined Iowa and Columbia cohorts:
682 of the cases did not have the protective factors (74.78%), 230 did.
204 of the controls had the protective factors (55.74%), 162 did not.

Table 13 shows the statistics for each cohort. The GA performed well across the board. Overall, those with the protective factors described by the model were 3.6581 times less likely to get AMD than those without the protective factors.

Given the clear statistical difference in several key SNP's between the two cohorts, finding a single model that would more accurately predict outcomes/protection was a challenge for both humans and machine learning alike. The hand built model performed admirably, and interestingly identified the identical heterozygous pairing of SNP's that the GA did (RS547154 as AB, RS4151667 as AB), including the same OR'ing together of those SNP's.

Despite the difficulty of the task, the GA performed well on the out of sample test (Fishers Iowa p<0.0000749). The GA outperformed the hand built model on all cohorts. Nonetheless, the hand built model does a very adequate job of predicting outcomes. Other variants of this model were tested but were unable to improve on its performance. Given the many possible combinations of SNP's/Genotypes/logical operators, this is to be expected and hence the value of the machine learning approach which can test 10's of thousands of model variations within a reasonable timeframe.

Given the highly statistical significance of the single SNP (RS1061170 as T/T: $x2=97.25$), one might conclude that by itself it can predict risk for AMD. In order to test whether the single SNP or the multi-loci models would have potential suitability for prediction of protection in the general population, permutation testing was conducted on the data. The Permutation testing showed that the single SNP was much more likely to produce a statistically significant result with random mixing of the data than either the GA or hand built models with a mean chi square score of 4.8153 over 3000 permutations versus, 3.3157 for the GA and 1.2207 for the hand built. On the Odds Ration evaluation, the single SNP had 625 permutations with an OR>1.5 versus 133 for the GA model and 46 for the hand built model. The hand built model simply represents of combination of genotypes that is rarely occurring in any sample. On balance, the GA model exhibited the best true case control performance and permutation results.

When the model statistics, ROC plots and permutation tests are looked at collectively, it appears that the multi-loci model approach to predict outcomes is superior to any single loci across diverse groups.

CONCLUSION

In conclusion, this study extends and refines the role of the alternative complement pathway in the pathobiology of AMD and further strengthens the proposed model that infection and/or inflammation play a major role in this common disease (Hageman et al., 2005, supra; Anderson et al., 2002, supra; Hageman et al., 2001, supra).

TABLE 13

| | Genetic Algorithm Derived Model Statistics | | | | | |
|---|---|---|---|---|---|---|
| | Iowa & Columbia | | Columbia | | Iowa | |
| | Score | Value | Score | Value | Score | Value |
| Fishers | | P = 1.689e−23 | | P = 2.974e−22 | | P = 0.0000749 |
| Odds Ratio | | 3.6581 | | 4.727 | | 2.2512 |
| | | Std Error: 0.4792 | | | | |
| | | 95% CI 2.8298 < OR < 4.7288 | | | | |
| | | Inverse OR: .27 | | | | |
| Chi Square | 103.128 | P = 3.141E−24 | 96.451 | P = 9.148E−23 | 13.17 | P = 0.00028 |
| Yates | 101.801 | P = 6.138E−24 | 94.886 | P = 2.016E−22 | 12.34 | P = 0.00044 |

Example 3

Administration of Protective BF or C2 Protein to Prevent Development of AMD

A subject presents with signs and/or symptoms of AMD, including drusen. The subject tests negative for the protective polymorphisms R32Q and L9H in BF, and IVS 10 and E318D in C2. It is recommended that the subject be treated with protective BF protein (having the R32Q polymorphism). The subject is administered intravenously an amount of protective BF in aqueous saline sufficient to bring the serum concentration of BF to between 9 and 31 mg/dL, once a month for six months. At this time, the subject is monitored for drusen as well as the presence of other signs and/or symptoms of AMD. If the signs and/or symptoms of AMD have not progressed, administration of protective BF is continued, once a month indefinitely, with monitoring of the clinical status of the patient as frequently as indicated, but at least once every six months.

In other clinical regimens, the protective BF protein is administered intranasally once each day to provide more sustained exposure to the protective effects of the protein.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

In view of the many possible embodiments to which the principles of our invention may be applied, it should be recognized that the illustrated embodiment is only a preferred example of the invention and should not be taken as a limitation on the scope of the invention. Rather, the scope of the invention is defined by the following claims. We therefore claim as our invention all that comes within the scope and spirit of these claims.

The invention claimed is:

1. A method for assessing the risk of development of, or likely progression of, age-related macular degeneration (AMD) in a human subject, the method comprising determining whether the subject carries one or more of:
   a) A or G at rs641153 of the complement factor B (BF) gene, or R or Q at position 32 of the BF protein;
   b) A or T at rs4151667 of the BF gene, or L or H at position 9 of the BF protein;
   c) G or T at rs547154 of the C2 gene; and
   d) C or G at rs9332739 of the C2 gene, or E or D at position 318 of the C2 protein.

2. The method of claim 1 further comprising determining whether the subject carries one or more of:
   a) delTT in the complement factor H (CFH) gene; and
   b) C or T at rs1061170 of the CFH gene, or Y or H at position 402 of the CFH protein.

3. The method of claim 1, wherein the subject is asymptomatic of age-related macular degeneration.

4. The method of claim 1, wherein the subject has symptoms of age-related macular degeneration.

5. The method of claim 1 comprising detecting a genotype from a cell of the subject.

6. The method of claim 5 further comprising determining whether the subject is homozygous or heterozygous for a said polymorphism.

7. The method of claim 1 comprising detecting a protein variant in the subject.

8. The method of claim 1 comprising detecting mRNA from a cell of the subject.

9. The method of claim 1 comprising the step of obtaining a biological sample from a human subject.

10. The method of claim 9, wherein the sample is a body fluid.

\* \* \* \* \*